(12) United States Patent
Najafi et al.

(10) Patent No.: US 10,692,603 B2
(45) Date of Patent: Jun. 23, 2020

(54) METHOD AND SYSTEM TO IDENTIFY FRAILTY USING BODY MOVEMENT

(71) Applicant: THE ARIZONA BOARD OF REGENTS ON BEHALF OF THE UNIVERSITY OF ARIZONA, Tucson, AZ (US)

(72) Inventors: Bijan Najafi, Tucson, AZ (US); Martha Jane Mohler, Tucson, AZ (US); Nima Toosizadeh, Tucson, AZ (US)

(73) Assignee: THE ARIZONA BOARD OF REGENTS ON BEHALF OF THE UNIVERSITY OF ARIZONA, Tucson, AZ (US)

(*) Notice: Subject to any disclaimer, the term of this patent is extended or adjusted under 35 U.S.C. 154(b) by 719 days.

(21) Appl. No.: 14/711,181

(22) Filed: May 13, 2015

(65) Prior Publication Data

US 2015/0332004 A1 Nov. 19, 2015

Related U.S. Application Data

(60) Provisional application No. 61/992,397, filed on May 13, 2014.

(51) Int. Cl.
G16H 50/30 (2018.01)
G16H 50/20 (2018.01)

(52) U.S. Cl.
CPC ............. *G16H 50/30* (2018.01); *G16H 50/20* (2018.01)

(58) Field of Classification Search
CPC ........................... G06F 19/3431; G06F 19/345
See application file for complete search history.

(56) References Cited

U.S. PATENT DOCUMENTS

| 7,764,990 B2 * | 7/2010 | Martikka ............. A61B 5/0488 600/520 |
| 2009/0076364 A1 | 3/2009 | Libbus |
| 2011/0208444 A1 * | 8/2011 | Solinsky ............... A61B 5/112 702/41 |
| 2011/0288811 A1 | 11/2011 | Greene |

(Continued)

OTHER PUBLICATIONS

Theou et al., "Daily muscle activity and quiescence in non-frail, pre-frail, and frail older women", Experimental Gerontology 45 (2010) 909-917.*

(Continued)

*Primary Examiner* — Robert A Cassity
*Assistant Examiner* — Tsu-Chang Lee
(74) *Attorney, Agent, or Firm* — Stuart H. Mayer; Mayer & Williams PC

(57) ABSTRACT

Systems and methods are disclosed which provide a way to diagnose frailty using an upper extremity (and/or other body portions) frailty assessment. Within this method, several parameters can be calculated based on the kinematics (e.g., pure motion without including forces) and kinetics (e.g., analysis of forces and moments) of, for example, joint flexion/extension. An ordinal and/or continuous frailty score can be determined based on calculated markers of frailty, such as slowness, weakness, flexibility, and/or exhaustion, while performing a short-duration upper extremity task. Patients can be classified as non-frail, pre-frail, or frail.

43 Claims, 10 Drawing Sheets

(56) References Cited

U.S. PATENT DOCUMENTS

| | | | | |
|---|---|---|---|---|
| 2013/0274587 | A1* | 10/2013 | Coza | A61B 5/6804 600/409 |
| 2013/0338802 | A1* | 12/2013 | Winsper | G06F 19/3481 700/92 |
| 2014/0243696 | A1 | 8/2014 | Kimmel | |
| 2014/0336947 | A1* | 11/2014 | Walke | A61B 5/1121 702/19 |
| 2015/0223743 | A1* | 8/2015 | Pathangay | A61B 5/18 600/301 |

OTHER PUBLICATIONS

Bigland-Ritchie, et al., "Conduction velocity and EMG power spectrum changes in fatigue of sustained maximal efforts", American Physiological Society, 1981.*

Farina, et al., "Assessment of Average Muscle Fiber Conduction Velocity From Surface EMG Signals During Fatiguing Dynamic Contractions", IEEE Transactions on Biomedical Engineering, vol. 51, No. 8, Aug. 2004 (Year: 2004).*

Polanczyk CA, Marcantonio E, Goldman L et al. Impact of age on perioperative complications and length of stay in patients undergoing noncardiac surgery. Ann Intern Med 2001; 134:637-643.

Makary MA, Segev DL, Pronovost PJ et al. Frailty as a predictor of surgical outcomes in older patients. J Am Coll Surg 2010; 210:901-908.

Davenport DL, Bowe EA, Henderson WG et al. National Surgical Quality Improvement Program (NSQIP) risk factors can be used to validate American Society of Anesthesiologists Physical Status classification (ASA PS) levels. Ann Surg 2006; 243:636-644.

Fried LP, Tangen CM, Walston J et al. Frailty in older adults: Evidence for a phenotype. J Gerontol a Biol Sci Med Sci 2001; 56A:M146-M156.

Rockwood K, Andrew M, Mitnitski A. A comparison of two approaches to measuring frailty in elderly people. J Gerontol A Biol Sci Med Sci 2007;62A:738-743.

Rockwood K, Song X, MacKnight C et al. A global clinical measure of fitness and frailty in elderly people. Can Med Assoc J 2005; 173:489-495.

Toosizadeh N, Mohler J, Najafi B. Assessing Upper Extremity Motion: An Innovative Method to Identify Frailty. JGS 2015; Manuscript No. 13451.

Kubicki A, Bonnetblanc F, Petrement G, Ballay Y, Mourey F. Delayed postural control during self-generated perturbations in the frail older adults. Clin Intery Aging. 2012; 7: 65-75.

Folstein MF, Folstein SE, McHugh PR. 'Mini-mental state'. A practical method for grading the cognitive state of patients for the clinician. J Psychiatr Res 1975; 12:189-198.

Fried, et al, "Untangling the concepts of disability, frailty, and comorbidity: implications for improved targeting and care" Journal of Gerontology: Medical Sciences, 2004, vol. 59, No. 3, 255-263 (9 pages total).

G. Abellan Van Kan, et al. "The I.A.N.A. Task Force on Frailty Assessment of Older People in Clinical Practice" The Journal of Nutrition, Health & Aging© vol. 12, No. 1, 29-37, 2008 (9 pages total).

N.M. de Vries, et al. "Outcome instruments to measure frailty: A systematic review", Ageing Research Reviews 10 (2011) 104-114 (11 pages total).

Cooper R., Kuh D, Hardy R., "Objectively measured physical capability levels and mortality: systematic review and meta-analysis" BMJ 2010; 341:c4467 (12 pages total).

G. Abellan Van Kan, et al., "Gait Speed At Usual Pace As a Predictor of Adverse Outcomes in Community-Dwelling Older People an International Academy on Nutrition and Aging (IANA) Task Force" JThe Journal of Nutrition, Health & Aging© vol. 13, No. 10, 881-889 (10 pages total).

Moscato BS, et al., "Validation of a modified center for epidemiologic studies depression (CES-D) scale with a one-month time frame" American Journal of Epidemiology. 1998; 147(11): 218-218 (2 pages total).

Bijan Najafi, Ph.D., M.Sc., et al. "Novel Wearable Technology for Assessing Spontaneous Daily Physical Activity and Risk of Falling in Older Adults with Diabetes" Journal of Diabetes Science and Technology vol. 7, Issue 5, Sep. 2013, 1147-60 (14 pages total).

* cited by examiner

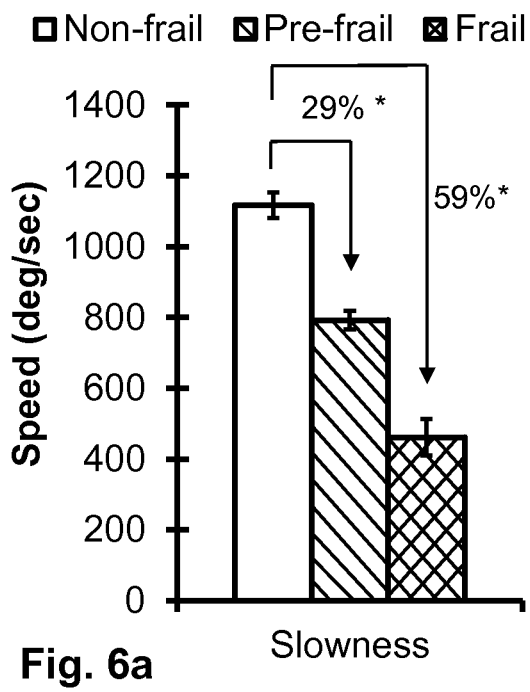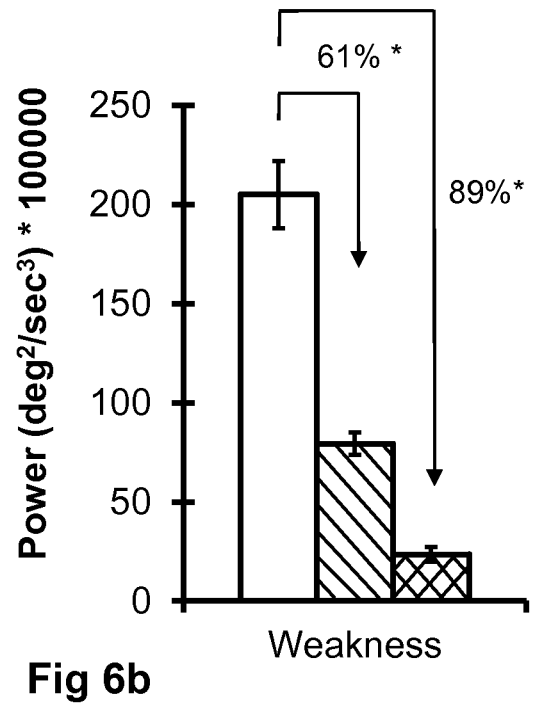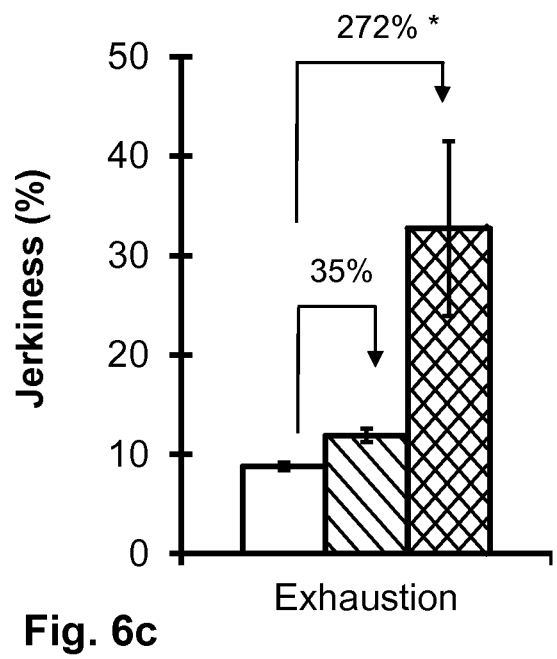

METHOD AND SYSTEM TO IDENTIFY FRAILTY USING BODY MOVEMENT

CROSS-REFERENCE TO RELATED APPLICATIONS

This application claims benefit of priority of U.S. Provisional Patent Application Ser. No. 61/992,397, filed May 13, 2015, and entitled "Method and System to Identify Frailty Using Joint Movement Protocol", which is owned by the assignee of the present application and herein incorporated by reference in its entirety.

GOVERNMENT LICENSE RIGHTS

This invention was made with Government support under Grant No. R42 AG032748 awarded by NIH. The government has certain rights in the invention.

FIELD

This disclosure generally relates to body movement monitoring systems, and more particularly to systems that relate to measuring and evaluating frailty in patients, including non-ambulatory patients.

BACKGROUND

Older adults are at a high risk of disability, long term hospitalization, unfavorable discharge disposition, and death after injury, but age itself is a poor indicator of risk due to the heterogeneity of older adults [1-3]. The concept of "frailty" is used to identify homeostenotic older adults with low physiological reserves and vulnerability to illness and other stressors. Such patients also have alterations in energy metabolism, decreased skeletal muscle mass and quality, and altered hormonal and inflammatory functions. Frailty is associated with excess functional decline, dependency, disability, increased healthcare utilization, hospitalization, institutionalization, and death [4-5].

The geriatric syndrome of "frailty", i.e., "frailty syndrome" or "FS", is one of the greatest challenges facing our aging population, and is associated with adverse health outcomes, dependency, institutionalization and mortality. National population projections from the US Census Bureau estimate that by 2050 the number of older adults (e.g., >65 years old) in the US will double. Frailty prevalence increases with age, with up to 30% of the population meeting frailty criteria by age 90 [4]. Thus, the US population of (frail) elders is rapidly growing. Health care utilization and associated costs among this population account for a disproportionate percentage of US health care costs. In geriatric care, prevention, early diagnosis, intervention and management of frailty are critical and growing challenges.

Beyond the geriatric population, frailty as a clinical syndrome has also been observed in certain younger patients. In particular, those with underlying chronic viral infections, such as HIV, have been found to be frail. Similarly, patients with chronic renal insufficiency who are on dialysis have been diagnosed as frail, as well as adult survivors of childhood cancers. FS is becoming increasingly recognized as a distinct clinical syndromic state in a wide range of patients over a wide range of ages.

This Background is provided to introduce a brief context for the Summary and Detailed Description that follow. This Background is not intended to be viewed as limiting the claimed subject matter to implementations that solve any or all of the disadvantages or problems presented herein.

SUMMARY

There is increasing evidence that assessing frailty facilitates optimal medical decision-making. However, currently available approaches for identifying frailty have several limitations. Specifically, they are clinically cumbersome and time-consuming (e.g., the Rockwood Frailty Index [6]), or they are based on gait-centered measures, (e.g., the Fried Frailty Criterion [4]) that are not useful for mobility-impaired or bedbound patients.

Risk stratification based on frailty can help contribute to better informed treatment, management and discharge strategies, and optimized outcomes in these growing populations. An unmet need exists in developing devices, methods and systems to diagnose frailty, determine its stage and severity, monitor its status and/or change over time, and differentiate it from other debilitating diseases or from simple age-related functional declines. Moreover, an unmet need exists in developing devices, methods and systems to diagnose frailty in mobility challenged patients, such as those for whom gait analysis is not possible.

Systems and methods according to present principles provide ways to identify frailty using, in one implementation, a combination of wearable sensors, a test protocol, and a movement quality assessment method. The systems and methods according to present principles may then be employed to compute markers (e.g., parameters) of frailty, which may include the following: 1) slowness, 2) weakness, 3) exhaustion, 4) flexibility, and 5) muscle activation patterns, e.g., muscle conductivity velocity, muscle activation map, muscle activation delay, muscle activation pattern in response to external load or external distraction, and the like. An exemplary method to score each measured parameter and to combine them to identify a continuous frailty score or an ordinal frailty status (e.g., non-frail, pre-frail, or frail) is described. Pre-frailty may be identified when there are fewer markers of frailty compared to a frail individual and/or when a continuous frailty score is lower than a frailty threshold but higher than a non-frailty threshold. More specifically, the systems and methods allow classification between non-frail and pre-frail, and between pre-frail and frail individuals. The foregoing and other frailty characteristics, variables, measurements, calculations, and/or the like described herein can be considered frailty information associated with the systems and methods described herein.

Systems and methods in certain implementations provide significant advantages, including providing a sensitive and specific measure of frailty that does not necessarily rely upon gait parameters. The systems and methods are useful for older adults in emergency, trauma, and surgical settings, where walking speed may not be easily measured in injured or bedbound patients. Further, the systems and methods may also be advantageous for quick and easy analysis of frailty in the home or outpatient clinical setting. The systems and methods may take advantage of measurements at the extremities, e.g., upper extremities, and thus may not require gait analysis.

Other advantages according to certain implementations of the embodiments disclosed herein may include one or more of the following: the systems and methods may advantageously employ low cost sensors; the measurements and analysis may be easily and conveniently performed in under a minute; the systems and methods are applicable and easy to use on older non-ambulatory patients; and lower wage medical assistants may easily administer the test.

The systems and methods may achieve similar results as compared with a "gold standard", e.g., the Fried Frailty Criteria, which stratifies patients into frailty categories, using standard criteria, e.g., unintentional weight loss, self-reported exhaustion, weakness (grip strength), slow walking speed, and low physical activity. In one implementation, and in a study that is described in detail below (also refer to [7]), data were entered into the Johns Hopkins frailty calculator and compared to population norms. Individuals with three or more positive frailty criteria were considered "frail", those with one or two frailty criteria were considered "pre-frail", and those with none of the above criteria were considered "non-frail". The stratifications according to the system and method showed favorable comparisons with the Fried Frailty Criteria, as described in greater detail below.

Other specific advantages of the systems and methods compared to conventional approaches to frailty assessment may also be seen. For example, in the Fried Frailty Criterion, hand grip strength is one of the five criteria for frailty assessment. This requires six maximum grip strength measurements (three for each hand). In contrast, tests according to current principles according to certain embodiments are shorter in duration, less strenuous and cover several frailty markers in addition to weakness. Moreover, all the parameters derived from the tests described here provide higher effect sizes compared to individual grip strength in identifying frailty.

In contrast to existing techniques, the systems and methods according to present principles include a pre-frail categorization and provide a methodology for identifying frailty that involves arm movement in a seated or supine position. As another exemplary advantage according to certain implementations of the present principles, it is noted that in another study [8] that involved arm motion for identifying frailty, participants were asked to perform rapid focal arm-raising movement pointing to a stimuli in a standing posture, while their balance was assessed using a force-measuring platform. According to the results of this study, a slower hand movement was observed in the frail group compared to a healthy sample; however, the pre-frail category was not evaluated in this study. The systems and methods according to present principles include pre-frail categorization and provide a means for identifying frailty that involves arm movement in a seated or supine position.

As another exemplary advantage according to certain implementations of the present principles, it is noted that assessment of gait, weakness, exhaustion, and joint flexibility are helpful measures for quantifying health status, risk of falling, cognitive decline, and the like. However, current methods often required that a patient walk a few steps. This may not be practical for mobility-impaired patients. This may also not be practical for use in homes or clinics where there may not be enough room for such examinations or where management of risk would be difficult due to the presence of obstacles and distractions or limited manpower resources to administer walking tests while maintaining the safety of the patient during walking According to certain implementations, the present systems and methods may predict walking speed in normal and cognitively challenged (e.g., dual task) conditions. This would be highly beneficial and could be used for identifying patients at risk of falling, evaluating health status, or tracking outcomes post intervention. Other potential applications of the present principles could be tracking recovery of patients for decision making about discharge, assessing the risk of readmission, predicting adverse events, evaluating responses to medications or interventions, identifying delirium or other in-hospital complications, and evaluating a patient's risk for not tolerating a specific surgical operation.

Other advantages will be apparent from the description that follows, including the figures and claims.

This Summary is provided to introduce a selection of concepts in a simplified form. The concepts are further described in the Detailed Description section. Elements or steps other than those described in this Summary are possible, and no element or step is necessarily required. This Summary is not intended to identify key features or essential features of the claimed subject matter. The claimed subject matter is not limited to implementations that solve any or all disadvantages noted in any part of this disclosure.

BRIEF DESCRIPTION OF THE DRAWINGS

The foregoing and other features of the present disclosure will become more fully apparent from the following description, taken in conjunction with the accompanying drawings. Understanding that these drawings depict only some embodiments in accordance with the disclosure and are, therefore, not to be considered limiting of its scope, the disclosure will be described with additional specificity and detail through use of the accompanying drawings.

FIGS. 6(a)-6(c) show differences between non-frail, pre-frail, and frail individuals (as identified using the Fried Frailty Criterion) in three markers of frailty derived according to an example embodiment of the present principles.

Elements are not drawn to scale unless otherwise noted. Like reference numerals refer to like elements throughout

DETAILED DESCRIPTION

Figure 1:
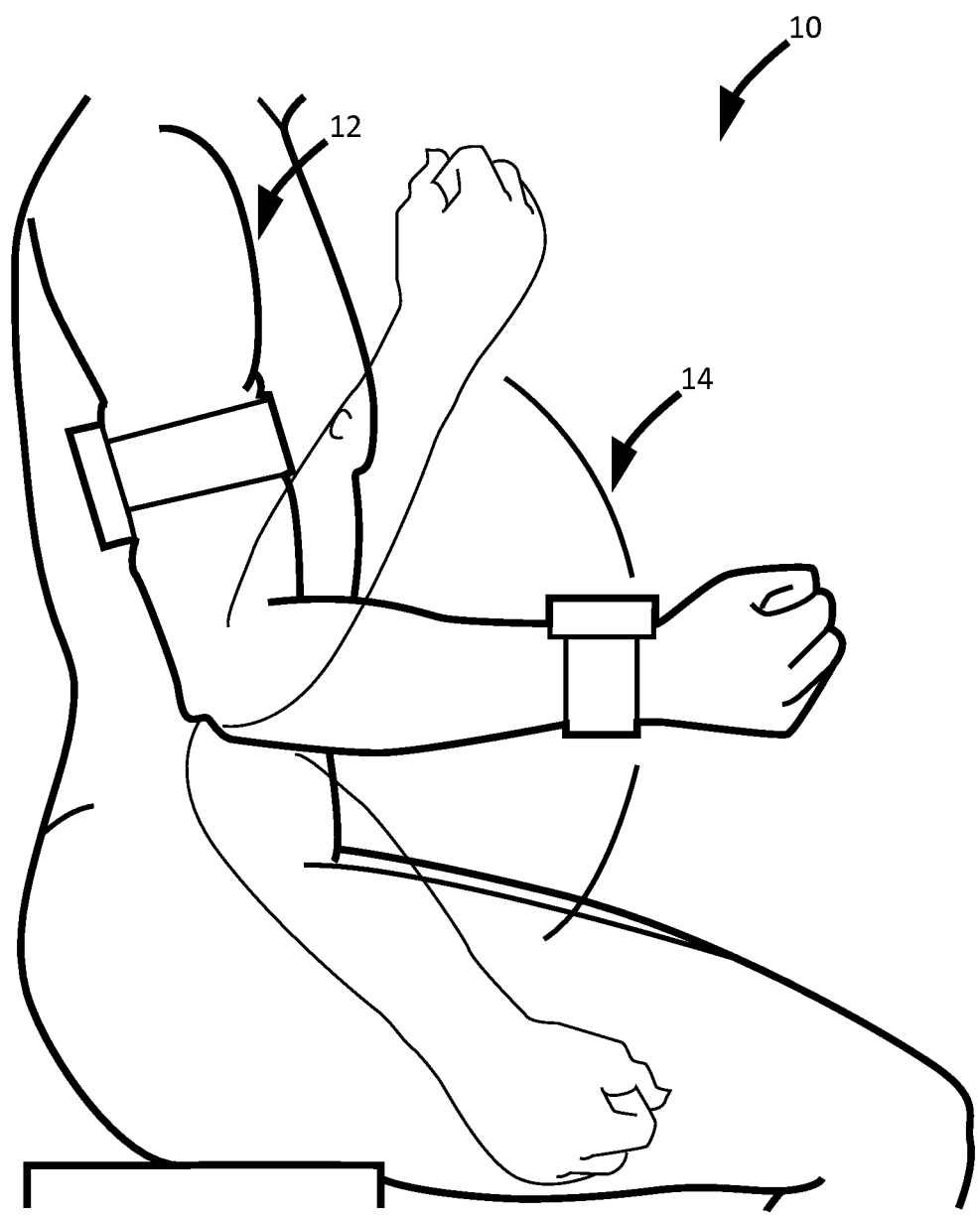
FIG. 1 schematically illustrates an example embodiment of a frailty evaluation system including two movement sensors attached to an upper arm and forearm of a patient to measure, for example, elbow angle, angular velocity, and/or elbow angular acceleration.

In the following detailed description, reference is made to the accompanying drawings, which form a part hereof. In the drawings, similar symbols typically identify similar components, unless context dictates otherwise. The illustrative embodiments described in the detailed description and drawings are not meant to be limiting. Other embodiments may be utilized, and other changes may be made, without departing from the spirit or scope of the subject matter presented here. It will be readily understood that the aspects of the present disclosure, as generally described herein, and illustrated in the figures, may be arranged, substituted, combined, and designed in a wide variety of different configurations, all of which are explicitly contemplated and made a part of this disclosure.

Systems and methods according to present principles include protocols useful in testing patients for frailty. The systems and methods include movement sensors to measure results of tests performed by a patient or person, and the systems and methods further provide ways to analyze the measured results to determine frailty status.

The physical tests according to present principles may be ones in which patients repetitively flex and extend a body joint, e.g., an elbow, to full flexion and extension angles as quickly as possible. As an example patients may perform a 50-second trial of elbow flexion/extension, divided into 20 seconds of elbow flexion of the right arm, 10 seconds rest, and then 20 seconds of elbow flexion of the left arm. While periods of other than 20 seconds may be used, the use of a period of 20-seconds of flexion may be especially useful, for upper extremities especially, as the same are based on pilot data indicating the time needed to capture alterations in elbow angular velocity due to exhaustion in healthy persons, to avoid ceiling effects. It is believed that for most older adults a test period of from about 10 to 30 seconds is appropriate for each side (for tests performed using flexion of the elbows or shoulders or any other body segment), separated by a rest period of about 5 to 30 seconds.

To capture data during the above test, a sensor system was devised that attached to one or more parts of the moving extremities. Referring to FIG. 1, a sensor system 10 may include a set of one or more movement sensors, including a movement sensor 12 attached to an upper arm and a movement sensor 14 attached to a forearm, e.g., with bands. The sensors may be wireless as shown or may alternatively provide a wired output. The sensors (or sets of sensors) may be placed on other extremities as well, including on the shoulders, neck, head, and the like. While a dual sensor system is illustrated in FIG. 1, in some implementations adequate data may be obtained from just one sensor, as will be described by way of example below.

The movement sensors themselves may be inertial sensors including accelerometers, gyroscopes, and the like. In one implementation, and in the example below, tri-axial gyroscope sensors were attached to the upper arm near the biceps and to the forearm near the wrist using an elastic band, and the same measured three-dimensional angular velocity of the upper arm and forearm body segments, from which the angular velocity of the elbow can easily be derived. In this implementation, the sensors had a sampling frequency of 100 Hz, and constituted sensors sold under the trade name BalanSens™, available from BioSensics LLC of Cambridge, Mass. Techniques other than using gyroscopes may be employed, and in certain embodiments the sensors may not be worn by the patient. For example, the movement sensor(s) may be cameras (e.g., camera based motion capture) or the movement sensor(s) may be goniometers. In these cases, joint angles may be measured and then used to determine joint rotational velocities (e.g., by differentiation). Similarly, the movement sensor(s) may be accelerometers. In this case, rotational acceleration of a body segment may be derived, with certain assumptions, from linear acceleration(s) measured using accelerometer(s) attached to the body segment, and then rotational acceleration of the body segment may be used to determine rotational velocities (e.g., by integration). In general, any movement sensor allowing direct or indirect measurement of at least angular velocities of a body joint may be employed, and it may be further beneficial if the same is capable of performing other measurements as well, including flexion angles and acceleration. Generally, so long as the measurement system is capable of measuring angle, velocity, or acceleration, the other variables may be calculated.

The sensor system 10 may generally constitute a sensing module (SM), which may be attached to the user's body for measuring body movements. In one implementation, the sensor module includes one to three gyroscope sensors. In one exemplary configuration, at least one gyroscope is configured to measure speed of rotation of a body segment during a pre-defined flexion-extension activity. The SM may also include other kinematic sensors, e.g. accelerometer, magnetometer, and the like, and muscle activity sensors, e.g., electromyographic (EMG) sensors, and other tracking sensors, e.g., camera based systems, laser sensors, and the like.

Figure 2:
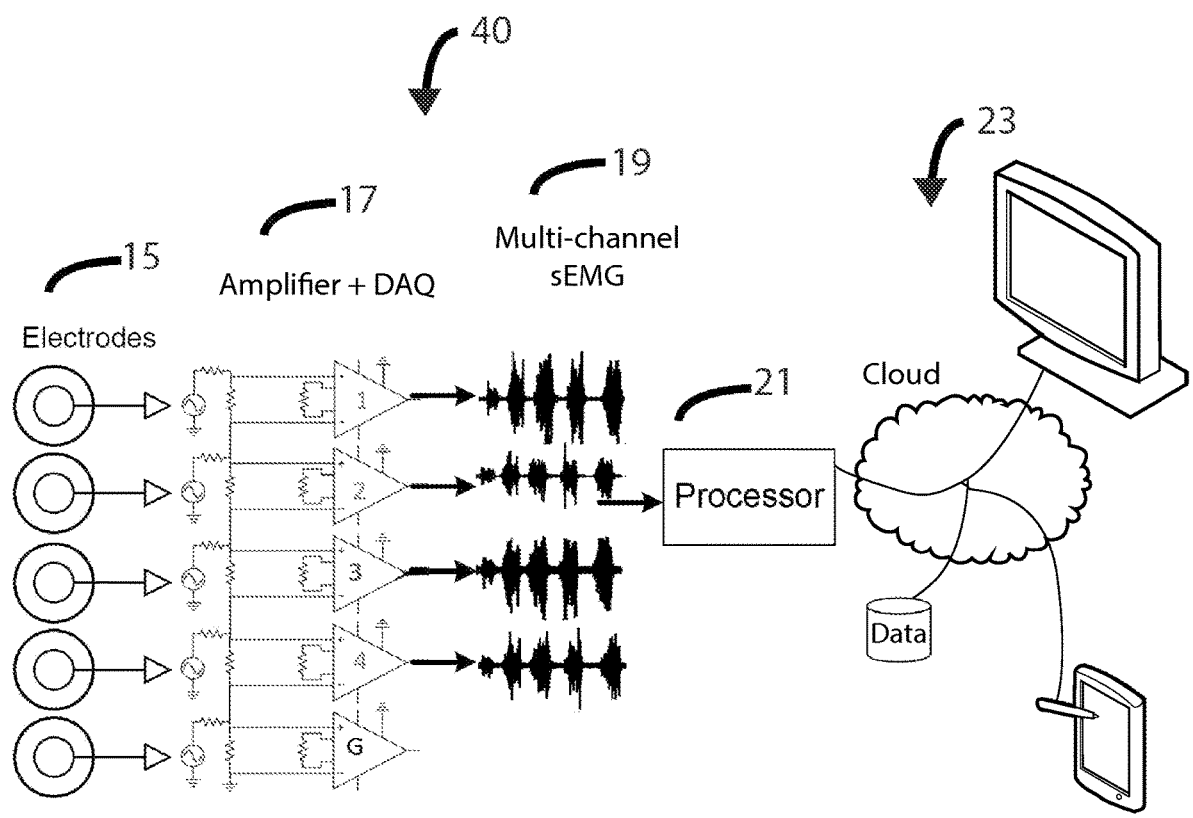
FIG. 2 illustrates an example embodiment of a multiple-channel electromyography (EMG) system to assess frailty.

An exemplary multiple channel surface EMG system is illustrated by the system 40 of FIG. 2, in which signals from electrodes 15 are amplified by an amplifier and data acquisition system 17, and fed into the multichannel surface EMG 19. The output of the multichannel surface EMG 19 is sent to a processor 21 and subsequently to a computing environment 23, which may include cloud or other storage and analysis means. That is, the SM may also include an on-board or remote data-storage system for storing the measured data. An optional on-board communications system provides the SM the capability to transmit the collected data and/or analyzed signals through either wired or wireless links for storage and/or further offline analysis. Data storage may include any type of memory such as static memory, random-access memory, or non-volatile memory. Other types of data storage will also be understood, including data storage on a means on the user for later transmission or downloading to a computing device.

Figure 3A:
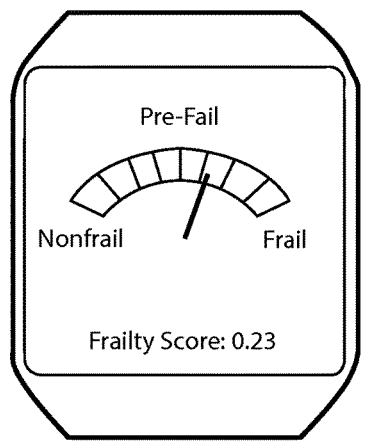
FIG. 3 illustrates an example embodiment of two exemplary methods for displaying frailty status.
Figure 3B:
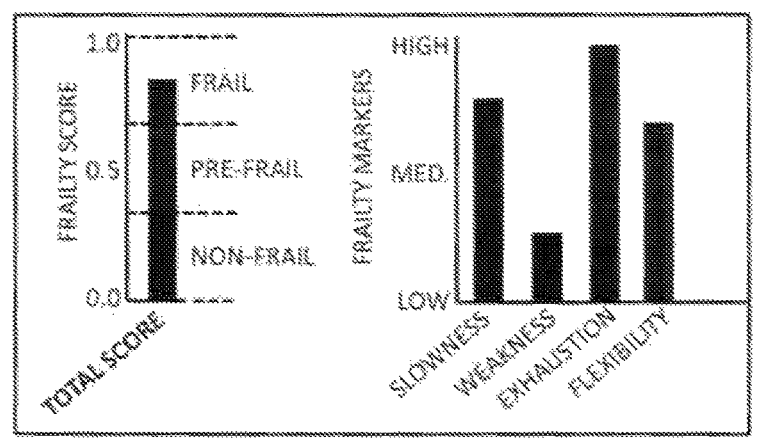

The system can display frailty status using an embedded multiple color LED or digital screen indicating the same. In addition, the system may remotely display relevant information such as frailty status (e.g., non-frail, pre-frail, frail), frailty score, history of frailty status, as well as status and history of each frailty marker, e.g., slowness, weakness, exhaustion, flexibility, muscle conductive velocity, muscle activation pattern, delay in muscle activation pattern, e.g., in response to a cue or to a command or to a distraction. Each of the measured parameters may be displayed either in a binary fashion, e.g., 0=healthy, 1=problem or unhealthy, or mapped to a scoring system, e.g., on a scale from 0 to 5, where a higher number indicates more deviation from a healthy status. The data can be transferred or communicated via Bluetooth®, Wi-Fi, or any other means of wired or wireless data communication. FIG. 3 illustrates an example embodiment of two exemplary methods for displaying frailty status. FIG. 3(a) illustrates an interface in the format of a watch that displays a frailty score. FIG. 3(b) illustrates another example in which a frailty score and its subcategories (e.g., markers of frailty), such as slowness, weakness, exhaustion, and flexibility, could be visualized.

Analysis of the measured signals may be carried out entirely on board the SM, partially on board the SM and partially at other location(s), or entirely at other location(s).

Several outcome measures representing kinematics and kinetics of elbow flexion may be derived using the data from the sensors, e.g., angular velocity data. Anthropometric data, e.g., height, weight, and the like, may also be used in the derivation of these outcome measures.

Figure 4:
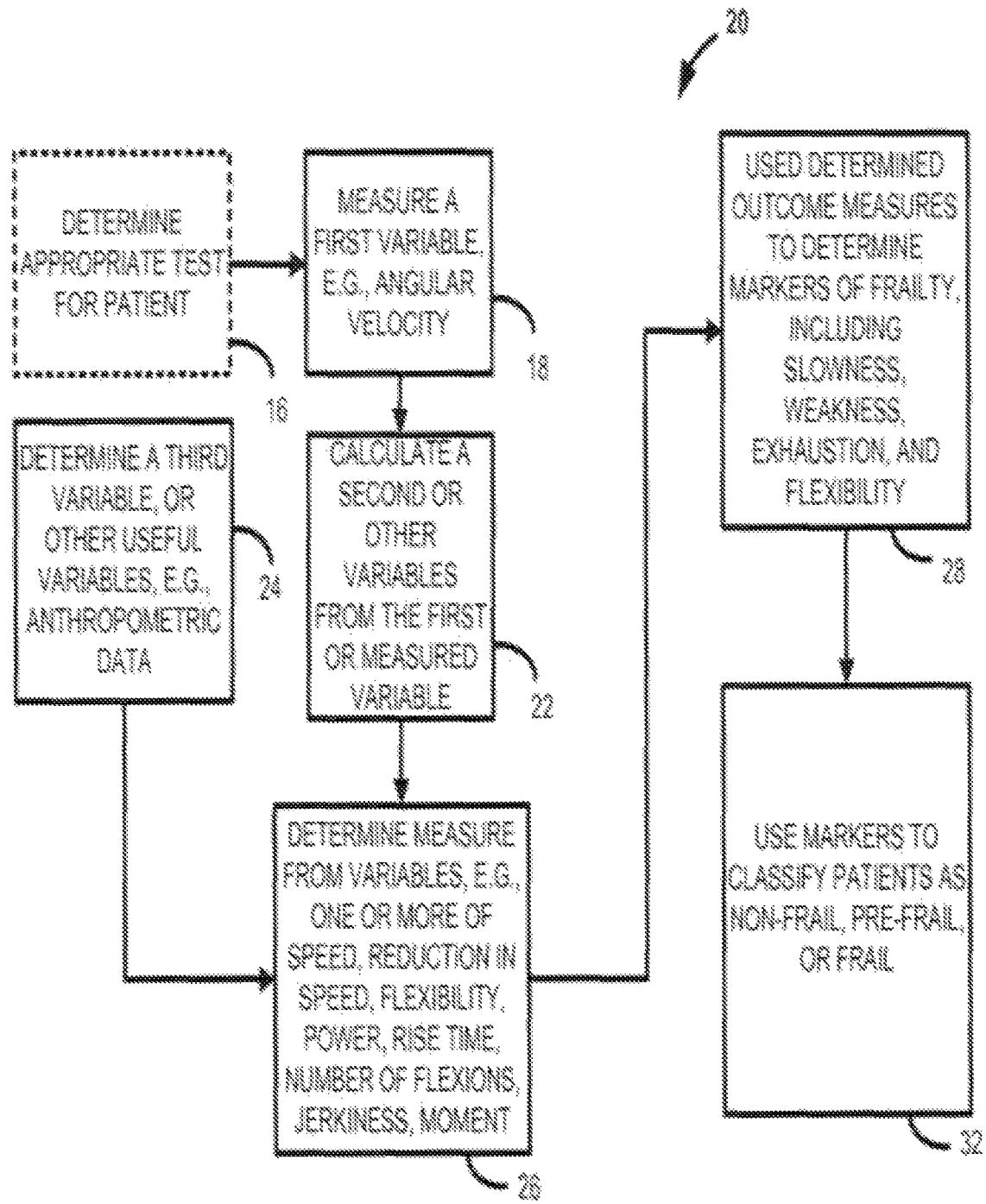
FIG. 4 illustrates an overview of an example embodiment of a method to determine a level of frailty, wherein the method excludes the use of electromyography.

In one exemplary method according to present principles, as illustrated by the flowchart 20 of FIG. 4, a first step, which is optional, is the protocol determination, e.g., determining the appropriate test useful in determining frailty for a given patient (step 16). A default protocol may be provided, and the default may be used in the absence of contravening indications. For example, an upper extremity (elbow flexion) test monitoring both arms may be a default, but a knee flexion test, or a single arm test, may be employed if the two arm test is contraindicated.

A next step is to perform the test and measure the appropriate variables (step 18). During the test angular velocity of the body segment (e.g., forearm, upper arm, or the like) may be measured by gyroscopes. Other variables may be calculated from the measured variable (step 22). For example, if angular velocity was measured, angular acceleration or angle may be calculated appropriately, e.g., via derivation or integration, respectively. It will be understood that other variables may also be measured, e.g., acceleration may be measured by an accelerometer or position may be measured by a camera-based motion capture system, and used to derive angular velocity, e.g., via derivation or integration.

Other variables may be determined and employed by means other than the sensors (step 24). For example, anthropometric data, such as the patient's height, weight, BMI, or the like, may be determined by any means and used as inputs according to the systems and methods.

Outcome measures may then be determined from the measured variables, the calculated variables, and the other variables (step 26). The determined outcome measures may then be employed to determine markers of frailty, including slowness, weakness, exhaustion, and flexibility (step 28). In particular, in a very specific implementation, slowness may be assessed by measuring speed and rise time; weakness may be assessed in another very specific implementation by measuring power and moment; exhaustion may be assessed in another very specific implementation by analysis of jerkiness and speed reduction. In addition, flexibility may be measured within this approach, as another frailty feature.

It will be understood that not all outcome measures need be considered in a given implementation, and that the particular outcome measures selected may vary from implementation to implementation. In addition, while the above markers of frailty are suggested to be derivable from certain outcome measures, it will be understood that other outcome measures may be employed in addition to or in lieu of the suggested measures.

In a final step, the determined markers may then be employed to classify frailty according to an ordinal (e.g., non-frail, pre-frail, or frail) and/or a continuous (e.g., 1-10) scale (step 32).

Figure 5:
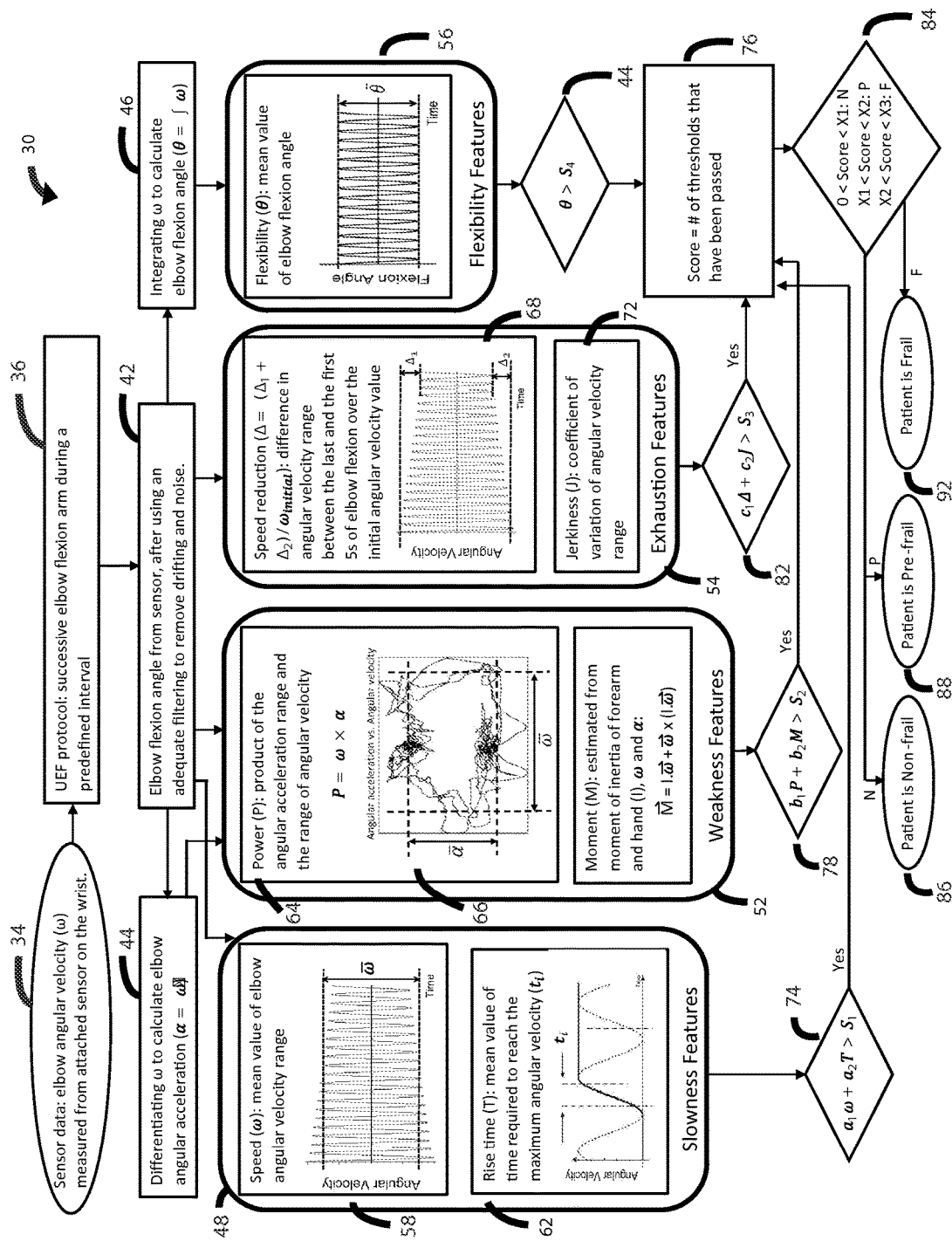
FIG. 5 illustrates in detail an example embodiment of a method to determine a level of frailty, wherein the method excludes the use of electromyography.

A more detailed method is illustrated by the flowchart 30 of FIG. 5. In this flowchart, a first step is the obtaining of sensor data, e.g., elbow angular velocity data ($\omega$), as measured from the attached sensor(s) (step 34). For example, according to an upper extremity frailty ("UEF") assessment protocol, repeated elbow flexions are performed over a predefined duration, e.g., 10, 20, 30, 40, 50, or 60 seconds including the foregoing values and ranges bordering therein (step 36). The resulting data may be, elbow flexion angular velocity data, and the same may be modified, e.g., using filtering, to remove drift and/or noise (step 42). The angular velocity data may be differentiated to obtain angular acceleration ($\alpha$) data (step 44). In the same way, the angular velocity data may be integrated to obtain flexion angle ($\theta$) data (step 46).

The angle, angular velocity, and angular acceleration data may be used to obtain data about various markers of frailty, including obtaining of data about slowness (step 48), weakness (step 52), exhaustion (step 54), and flexibility (step 56), as described in more detail below.

The obtaining of data about slowness (step 48) may include the determination of speed (step 58) and rise-time (step 62). Speed ($\omega$) may in certain embodiments be calculated as the mean value of the elbow angular velocity range (maximum speed-minimum speed) for each flexion/extension repetition during, e.g., 20 seconds of repeated flexion/extension, as represented by $\bar{\omega}$ in the graph shown at step 58. Rise-time (T) may in certain embodiments be defined as the mean value of the time required to reach the maximum angular velocity for each flexion/extension repetition during, e.g., 20 seconds of repeated flexion/extension. For example the graph at step 62 shows elbow angular velocity for two flexion/extension repetitions. The value $t_i$ represents the rise time for one repetition. The rise time parameter (T) is the mean of rise times from all repetitions.

The obtaining of data about weakness (step 54) may include the determination of power (step 64) and moment (step 66). Power (P) may in certain embodiments be calculated by deriving the angular acceleration of the elbow ($\alpha$), determining the angular acceleration range (represented by $\bar{\alpha}$ in the graph shown at step 64) and the angular velocity range (represented as $\bar{\omega}$ in the graph shown at step 64) for each flexion/extension repetition during, e.g., 20 seconds of repeated flexion/extension, and then taking the mean value of the product of these ranges. Since this parameter is the product of velocity and acceleration, it is related to the power of movement. Moment (M) may in certain embodiments be defined as the mean value of the maximum moment for each flexion/extension repetition during, e.g., 20 seconds of repeated flexion/extension, where moment may be estimated from the moment of inertia of the forearm and hand (I), the elbow angular velocity ($\vec{\omega}$) and the elbow angular acceleration ($\vec{\omega}$) as follows:

$$\vec{M} = I \cdot \vec{\omega} + \vec{\omega} \times (I \cdot \vec{\omega})$$

According to certain embodiments, moment of inertia may be estimated from gender and/or anthropometric data of the patient.

The obtaining of data about exhaustion (step 54) may include a determination of speed reduction (step 68) and jerkiness (step 72). Speed Reduction ($\Delta$) may in certain embodiments be calculated as the difference in angular velocity range between the last and the first 5 seconds of elbow flexion (represented in the graph at step 68 by $\Delta_1 + \Delta_2$), as a percentage of initial angular velocity range ($\omega_{initial}$). Jerkiness (J) may in certain embodiments be defined as the coefficient of variation of angular velocity range for each flexion/extension repetition during, e.g., 20 seconds of repeated flexion/extension.

The obtaining of data about flexibility (step 56) may generally be related to the magnitude of joint motion ($\bar{\theta}$), e.g., to the mean value of the range of elbow flexion angle over consecutive flexion/extension repetitions.

In addition, in certain embodiment the total number of elbow flexions completed may be an outcome measure.

Returning to the slowness marker and referring to step 74 of FIG. 5, in one implementation, if a function of speed (ω) and rise-time (T), normalized by appropriate coefficients (e.g., $a_1$ and $a_2$), is greater than some predetermined threshold (e.g., $S_1$), then a determination may be made that the marker of slowness has been met, and the same may be entered as an input into the overall frailty score (step 76). In the same way, if a function of the power (P) and the moment (M), again normalized by appropriate coefficients (e.g., $b_1$ and $b_2$), is greater than a predetermined threshold (e.g., $S_2$ at step 78), then a determination may be made that the marker of weakness has been met, and the same may be entered as an input into the overall frailty score (step 76). Similarly, if a function of the speed reduction (Δ) and the jerkiness (J), again normalized by appropriate coefficients (e.g., $c_1$ and $c_2$), is greater than a predetermined threshold (e.g., $S_3$ at step 82), then a determination may be made that the marker of exhaustion has been met, and the same may be entered as an input into the overall frailty score (step 76). Finally, if flexibility ($\bar{\theta}$) is greater than a predetermined threshold (e.g., $S_4$ at step 44), then a determination may be made that the marker of flexibility has been met, and the same may be entered as an input into the overall frailty score (step 76).

According to certain embodiments, the frailty score may be related to the number of markers that have been met (step 76) and this may be translated into an ordinal frailty status (e.g., non-frail, pre-frail, or frail) (step 84). If the number of markers that have been met is between zero and a first predetermined threshold X1 (step 84), the patient may be diagnosed as non-frail (step 86). If the number of markers that have been met is between the first predetermined threshold X1 and a second predetermined threshold X2 (step 84), the patient may be diagnosed as pre-frail (step 88). If the number of markers exceeds the second predetermined threshold X2, or is between the second predetermined threshold X2 in the third predetermined threshold X3 (step 84), the patient may be diagnosed as frail (step 92).

According to another embodiment (not represented in FIG. 5), a continuous frailty score may be computed as a function of two or more frailty markers. This continuous score may be mapped to a scoring system, e.g., on a scale from 0 to 5, where a higher number indicates more deviation from a healthy status, and may also be mapped to an ordinal frailty status (e.g., non-frail, pre-frail, frail) using a method similar to step 84 in FIG. 5.

As examples of the results of such data obtained, FIGS. 6(a)-6(c) show differences between non-frail, pre-frail, and frail individuals (as identified using the Fried Frailty Criterion) in three markers of frailty derived according to an example embodiment of the present principles. FIGS. 7 (a) and 7 (b) show correlations between certain outcome measures derived according to an example embodiment of the present principles and certain performance measures common to state of the art frailty assessment procedures.

Other ways to determine markers of frailty from sensor(s) data, as well as other data, will also be understood by one of ordinary skill in the art, and the same are encompassed by present principles. For example, other predictors or risk factors of frailty, such as age, gender, involuntary weight loss, activity level, and the like, could be included in the function for determining the frailty score. These predictors or risk factors could be, for example, entered into the system manually, at any time, following on-screen prompts.

Other ways of employing markers of frailty to stratify or categorize patients will also be understood by one of ordinary skill in the art, and the same are encompassed by present principles.

One advantage of certain implementations according to present principles is that several frailty features can be taken into account. The systems and methods according to present principles can assess slowness, weakness, exhaustion, and flexibility, which are all related to frailty syndrome. In a study that is described in detail below (also refer to [7]), the slowness marker was observed to be more pronounced when comparing pre-frail to non-frail individuals. On the other hand, weakness was observed to be better at distinguishing frail from pre-frail individuals. More specifically, speed of elbow flexion was observed to show the largest effect size in distinguishing between non-frail and pre-frail individuals, and power of movement was observed to have the largest effect size for differentiating between pre-frail and frail individuals. As such, the systems and methods can stratify or categorize frailty with good accuracy by incorporating multiple and different markers. In a study that is described in detail below (also refer to [7]), the slowness marker was observed to be more pronounced when comparing pre-frail to non-frail individuals. On the other hand, weakness may be better at distinguishing frail from pre-frail individuals. More specifically, speed of elbow flexion may show the largest effect size in distinguishing between non-frail and pre-frail individuals, and power of movement may have the largest effect size for differentiating between pre-frail and frail individuals. As such, the method can predict pre-frailty and frailty with good accuracy by incorporating multiple and different markers.

The systems and methods according to present principles are thus able to stratify or categorize frailty with a high sensitivity and specificity, based on a quick and simple upper extremity test without requiring gait analysis.

The systems and methods according to present principles can also predict gait speed in normal and dual-task conditions, as well as an individual's performance on other strength assessment routines, e.g., grip strength and the like. For example, using speed (FIG. 5 step 58) and rise-time (FIG. 5 step 62) UEF outcome measures, a patient's 15 feet walking duration (as measured during the assessment of frailty according to the Fried Frailty Criterion) may be estimated using, for example, the following equation:

$$\text{15 feet walking duration} = (a \times \text{Rise time}) - (b \times \log(\text{speed})) + c$$

where a, b, and c, are constant values. As another example, using power (FIG. 5 step 64) and moment (FIG. 5 step 66) UEF outcome measures, a patient's grip strength may be estimated using, for example, the following equation:

$$\text{Grip strength} = (a \times \text{Moment}) + (b \times 10^{-2} \times \log(\text{Power})) + c$$

where a, b, and c, are constant values.

According to certain embodiments, UEF could be performed in normal (without distraction) and dual-task (performing UEF while performing a cognitive task) conditions to estimate the effect of dual-tasking on UEF performance. This may be used, for example, to assess cognitive decline or the ability of a patient to multi-task.

According to certain embodiments, the UEF assessment protocol can be completed using one extremity. In particular, one limitation of using arm movement in the older population is the high prevalence of upper extremity osteoarthritis and other less common musculoskeletal diseases. Although osteoarthritis in the upper extremities is less common than osteoarthritis in the lower extremities, the frailty assessment may be difficult to perform for some older adults. In cases where one upper extremity has limited mobility, due to medical immobilization, musculoskeletal disease, or any other cause, performing frailty assessment on one side (either right or left) may be preferred. In an example study, using frailty assessment data from one arm (20 seconds of elbow flexion) provided acceptable accuracy for measuring frailty. There was a slight difference in frailty assessment accuracy between right and left arms; likely resulting from performance with the non-dominant arm (70-90% of the world's population is right-handed). Overall, performing a 20-second frailty assessment with the right arm (or left, where dominant), generally provides similar accuracy as a two-sided frailty assessment.

According to certain embodiments, the systems and methods may involve measurement of both forearm and upper arm rotational velocity using, for example, gyroscope sensors on the wrist and upper arm. According to alternate embodiments the systems and methods may involve measuring forearm rotational velocity using, for example, a gyroscope on the wrist. In an example study, frailty was categorized (e.g., non-frail, pre-frail, frail) using measures of elbow rotational velocity derived from gyroscopes on the wrist and upper arm, as well as using measures of elbow rotational velocity derived from gyroscopes on the wrist (e.g., by assuming that the upper arm was stationary and therefore elbow rotational velocity was equivalent to forearm rotational velocity). Although frailty prediction quality was reduced when using one sensor for measuring elbow flexion, the differences were negligible. It was observed that participants kept their upper-arms steady during the elbow flexion task and that most of the motion resulted from the forearm rotation Thus, according to certain embodiments, a single device applied at the wrist may be employed to provide higher clinical acceptability and ease of use, as well as to reduce cost, compared to a two sensor system.

A study that was undertaken using systems and methods according to present principles to objectively identify frailty is described in the following (also refer to [7]). Participants included a convenience sample of 117 community dwelling older adults (age ≥65 years) with no major mobility or upper extremity disorders: 50 non-frail, 51 pre-frail, and 16 frail, as determined by the Fried Criteria (see Table 1 below for demographic information of participants). ANOVAs and Chi-square tests were performed to evaluate the differences in demographic parameters between frailty groups. The average age was significantly different between the three groups, with a greater age among frail participants. The average mini-mental state examination [9] scores were not significantly different between groups.

Table 1 below provides the mean (SD or percentage) values of participant demographic information and frailty criteria. The symbol * indicates a significant effect. Participants' classification was based on Fried Criteria.

| | Non-frail | Pre-frail | Frail | p-value | Effect Size |
|---|---|---|---|---|---|
| Number (% of total) | 50 (43%) | 51 (43%) | 16 (14%) | — | |
| Male (% of the group) | 9 (18%) | 15 (29%) | 1 (6%) | 0.08 | |
| Age (SD) (yr) | 75.3 (6.8) | 79.7 (8.7) | 85.4 (7.0) | <.001* | 0.45 |
| Stature (SD) (cm) | 159.3 (7.4) | 160.0 (8.3) | 156.6 (10.3) | 0.36 | 0.13 |
| Body mass (SD) (kg) | 68.3 (12.8) | 77.2 (20.6) | 75.3 (20.1) | 0.04* | 0.24 |
| BMI (kg/m$^2$) | 26.9 (4.6) | 30.1 (7.6) | 30.6 (6.5) | 0.02* | 0.27 |
| MMSE score (SD) | 29.1 (1.3) | 28.6 (1.5) | 28.6 (1.8) | 0.26 | 0.16 |
| Grip strength from Fried Index (SD) (kg) | 25.9 (6.2) | 22.7 (7.3) | 16.1 (5.8) | <.001* | 0.49 |
| 15 feet walking time from Fried Index (SD) (sec) | 4.7 (0.8) | 7.2 (2.4) | 16.1 (10.0) | <.001* | 1.02 |
| Number of Observed Fried Criteria | | | | | |
| Weight loss (% of group) | — | 3 (6%) | 3 (19%) | 0.01* | |
| Weakness (% of group) | — | 19 (37%) | 13 (81%) | <.001* | |
| Slowness (% of group) | — | 28 (55%) | 15 (94%) | <.001* | |
| Exhaustion (% of group) | — | 12 (24%) | 12 (75%) | <.001* | |
| Low activity (% of group) | — | 7 (14%) | 12 (75%) | <.001* | |

To accomplish the measurements, wireless sensors were attached to the upper-arm and forearm with bands, and subjects performed repetitive elbow flexion/extension for 20 seconds on each side. The protocol was explained to participants and they were encouraged only once, before elbow flexion, to do the task as fast as possible (participants were not encouraged to increase the velocity of arm movement during the task).

Validation of the data was performed using a motion capture system. Comparing elbow flexion measurement between the sensor system and the motion capture system it was observed mean RMSE and R values of 9.2 deg and 0.99 for slow and 9.5 deg and 0.99 for fast elbow flexion, respectively, across all trials. These results demonstrate accurate angle estimation and excellent correlation coefficients in measuring elbow angle using the devised system.

For all outcome measures, the mean values across right and left arms were quantified, using forearm and upper-arm sensors to estimate elbow angle. Further, the analysis was repeated for several conditions: 1) single arm: using data from either right or left arm (for each side the elbow angle was calculated using forearm and upper-arm sensors); 2) single sensor: elbow angle was estimated using forearm sensors, and results were averaged across left and right arms; and 3) single arm-single sensor: using data from a forearm sensor on the right arm.

Frailty markers (slowness, weakness, exhaustion, and flexibility) were extracted (FIG. 5 steps 48, 52, 54, and 56), and associations between parameters and Fried Frailty categories were examined. In more detail, the frailty parameters were compared between three frailty groups (defined using Fried Criterion) using separate analyses of variance (ANOVAs) with age and body mass index (BMI) as covariates; post-hoc Tukey HSD tests were performed for three pairwise comparison of parameters among frailty groups. Independent association between parameters and frailty was assessed using multivariate ordinal logistic regression model, considering frailty as the dependent variable and age and BMI as covariates. Nominal logistic regression models were used to determine the sensitivity and specificity of pre-frailty and frailty predictions using the parameters. Parameters with an association with frailty (p<0.05) were entered into each model.

Referring in particular to Table 2, from ANOVA analyses, all outcome measures extracted from the frailty assessment tests were significantly different between frailty groups. Results from Tukey HSD tests indicated that speed, power, rise time, and number of flexions were significantly different between non-frail and pre-frail individuals. On the other hand, and referring specifically to Table 2, speed, flexibility, rise time, moment, jerkiness, and speed reduction were significantly different between pre-frail and frail groups. Among the outcome measures, speed, power, and jerkiness showed the largest effect sizes. Speed of elbow flexion was 29% less among pre-frail compared to non-frail, and 42% less among frail compared to pre-frail groups. Power of movement was 61% less among pre-frail compared to non-frail, and 70% less among frail compared to pre-frail groups. Jerkiness was 35% greater in pre-frail compared to the non-frail group, and 175% greater in the frail group compared to the pre-frail group (FIG. 6 and Table 2).

Table 2, below, provides mean, SD, and ANOVA results for parameters for non-frail, pre-frail, and frail groups. The symbol * indicates a significant effect.

| Parameter | Group | Mean | SD | p-value (ES) | Groups † | Pairwide p-value (ES) | 95% CI | |
|---|---|---|---|---|---|---|---|---|
| Speed | Non-frail | 1117 | 247 | p = | N and P | <.001* (1.48) | 110 | 347 |
| (deg/sec) | Pre-frail | 792 | 187 | <.001* | N and F | <.001* (2.83) | 325 | 668 |
| | Frail | 461 | 215 | (1.05) | P and F | <.001* (1.64) | 120 | 416 |
| Flexibility | Non-frail | 134 | 22 | p = | N and P | <.01* (0.83) | −2 | 24 |
| (deg) | Pre-frail | 115 | 24 | <.001* | N and F | <.001* (1.99) | 20 | 58 |
| | Frail | 87 | 28 | (0.65) | P and F | <.001* (1.07) | 12 | 45 |
| Power | Non-frail | 205.1 | 116.3 | p = | N and P | <.001* (1.44) | 35.6 | 130.4 |
| (deg$^2$/sec$^3$) * | Pre-frail | 79.3 | 40.5 | <.001* | N and F | <.001* (2.19) | 55.4 | 192.1 |
| 100000 | Frail | 23.5 | 15.7 | (1.02) | P and F | 0.33 (1.82) | −18.4 | 99.8 |
| Rise Time | Non-frail | 26.0 | 4.5 | p = | N and P | 0.01* (1.05) | 9.9 | 0.5 |
| (sec) * 100 | Pre-frail | 32.6 | 7.7 | <.001* | N and F | <.001* (1.33) | 19.5 | 5.9 |
| | Frail | 43.6 | 18.1 | (0.65) | P and F | <.01* (0.79) | 13.4 | 1.6 |
| Moment | Non-frail | 59.5 | 26.4 | p = | N and P | <.01* (0.64) | −0.8 | 11.5 |
| (Nm) | Pre-frail | 43.6 | 23.4 | <.001* | N and F | <.001* (2.26) | 4.2 | 22.1 |
| | Frail | 15.4 | 8.1 | (0.65) | P and F | <.01* (1.61) | 0 | 15.6 |
| Jerkiness | Non-frail | 8.8 | 8.1 | p = | N and P | 0.48 (0.76) | 7.8 | −3.2 |
| (%) | Pre-frail | 11.9 | 5.1 | <.001* | N and F | <.001* (0.93) | 23.9 | 7.1 |
| | Frail | 32.7 | 36.3 | (0.65) | P and F | <.001* (0.80) | 20.6 | 5.9 |
| Speed | Non-frail | 1.7 | 5.1 | p = | N and P | 0.05 (0.81) | 7.9 | −3.5 |
| Reduction | Pre-frail | 7.4 | 8.5 | <.001* | N and F | <.001* (1.26) | 24.3 | 6.1 |
| (%) | Frail | 22.8 | 23.1 | (0.65) | P and F | <.001* (0.88) | 21.1 | 4.9 |
| Number of | Non-frail | 23.7 | 5.0 | p = | N and P | <.001* (1.14) | 1.4 | 6.2 |
| Flexion | Pre-frail | 18.5 | 4.1 | <.001* | N and F | <.001* (2.12) | 3.2 | 10.3 |
| | Frail | 13.4 | 4.7 | (0.78) | P and F | 0.02* (1.16) | −0.1 | 6.1 |

Figure 7A:
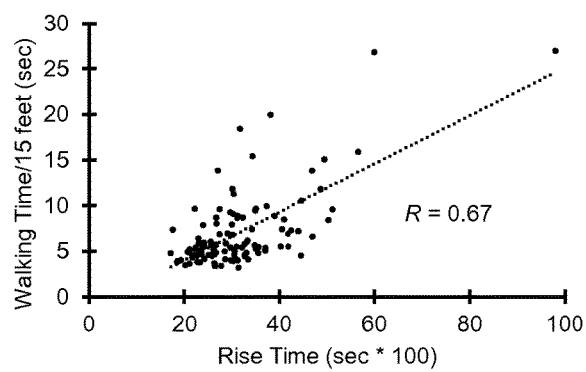
FIGS. 7(a) and 7(b) show correlations between certain outcome measures derived according to an example embodiment of the present principles and certain performance measures common to state of the art frailty assessment procedures.
Figure 7B:
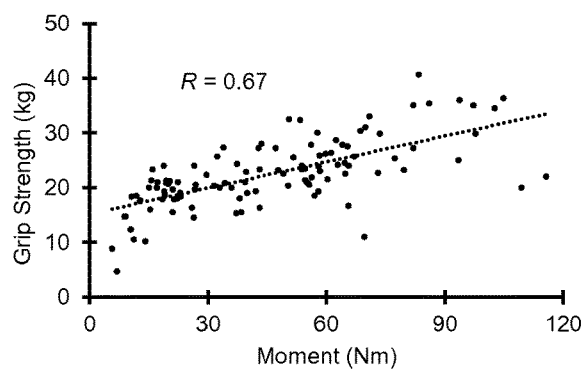

† N: non-frail, P: Pre-frail, and F: Frail
CI: Confidence Interval
ES: Effect Size Table 3 shows one-by-one correlation coefficients (R) between Fried Frailty Criteria and the UEF frailty outcome measures. The outcome measure with the highest correlation coefficient for 15 foot walking duration was rise time, and the outcome measure with the highest correlation coefficient for Grip Strength was moment. These correlations are shown in FIGS. 7(a) and 7(b), respectively.

| Correlation (R) | Speed | Flexibility | Power | Rise Time | Moment | Jerkiness | Speed Reduction | Number of Flexion |
|---|---|---|---|---|---|---|---|---|
| Walking Time/15 Feet | −0.59 | −0.38 | −0.43 | 0.67 | −0.41 | 0.58 | 0.60 | −0.56 |
| Grip Strength | 0.58 | 0.32 | 0.47 | −0.52 | 0.67 | −0.33 | −0.38 | 0.53 |

Using the frailty outcome measures, age, and BMI as independent variables in the logistic regression model, a sensitivity and specificity of 100% and 100% was achieved in predicting frailty. Similarly, in predicting pre-frailty, the respective values of sensitivity and specificity were 87% and 82%. These results suggest 49% and 110% improvement in respective frailty and pre-frailty predictions, compared to the condition where only age and BMI were used as independent variables.

As noted above, data may be obtained from just a single extremity instead of a pair. This configuration was tested in this exemplary study. In condition 1, where data from a single extremity was considered, a pre-frail categorical sensitivity and specificity of 85% and 83% was achieved when data from the right side was used. Corresponding values were 74% and 71% when left sided data were used. A frail categorical sensitivity and specificity of 100% and 100% was achieved with either right or left side elbow flexion data. In condition 2, where data from a single sensor was considered, sensitivity and specificity were 87% and 76% for the pre-frail and 100% and 100% for the frail. In condition 3, where data was considered from a single sensor and on a single arm, pre-frailty was predicted with 85% and 78% sensitivity and specificity, and frailty with 100% and 100% sensitivity and specificity.

In an alternate embodiment of the systems and methods, frailty can be evaluated based on muscle activation characteristics that can be measured using, for example, multi-channel EMG sensors located at predefined distances from each other. By placing EMG sensors in a predefined arrangement, e.g., by placing the sensors substantially equidistantly from each other, or at other such predefined common spacings, muscle fiber conductive velocity (MFCV) may be estimated. The estimation can occur by, e.g., measuring the distance between two peaks generated by cross-correlation of signals recorded by two electrodes located at the predefined distance.

Figure 8:
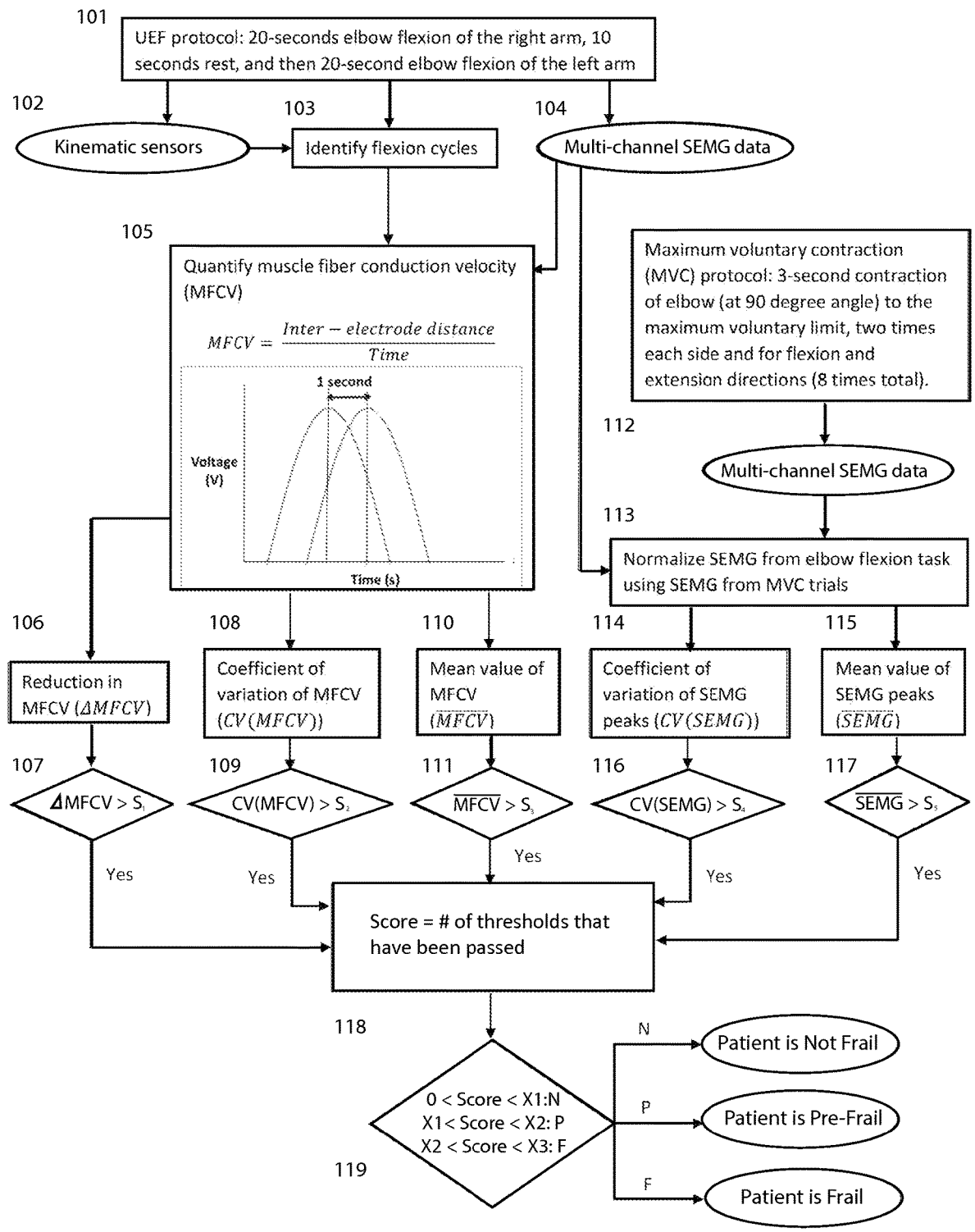
FIG. 8 illustrates in detail an example embodiment of a method used to determine a level of frailty, wherein the method includes the use of electromyography.

One exemplary method of evaluating frailty based in part on muscle activity patterns is described below, with reference to the flowchart in FIG. 8. Patients perform the previously described UEF protocol, which could be, for example, 20 seconds of elbow flexion of the right arm followed by 10 seconds of rest, followed by 20 seconds of elbow flexion of the left arm (step 101). The SM, e.g., gyroscope or other sensor, performs a measurement (step 102) and allows separation of body segment motions, e.g., flexion cycles (step 103). During each flexion cycle, MFCV is estimated (step 105) from multi-channel surface EMG data (step 104). The graph at step 105 shows two voltage peaks in surface EMG data recorded from two electrodes at a known distance from one another. The MFCV for each repetition is then defined as the known inter-electrode distance divided by the time difference between the peaks (e.g., 1 sec in the example graph at step 105). According to certain embodiments, to enhance the accuracy, the average of the MFCV is used, which is extracted from three or more EMG electrodes.

To identify frailty, changes in the pattern of MFCV during consecutive flexion-extension activities during a predefined interval, e.g., 20 seconds, may be estimated. This can be done in a number of ways, including by measuring the reduction in MFCV across multiple flexion cycles (step 106) and comparing to a threshold ($S_1$ at step 107), by measuring the coefficient of variation of measured MFCV during consecutive flexion cycles (step 108) and comparing to a threshold ($S_2$ at step 109), and/or by measuring the mean value of measured MFCV during consecutive flexion cycles (step 110) and comparing to a threshold ($S_3$ at step 111).

Frailty may also be characterized by 1) measuring a muscle activation pattern during a maximum voluntary contraction (step 112); 2) assessing the estimated muscle activation patterns across multiple EMG electrodes placed at the distances noted; and 3) normalizing (step 113). The assessment step may be performed by measuring the coefficient of variation of EMG peaks measured by each electrode (step 114) and comparing to a threshold ($S_3$ at step 116), and/or by measuring the mean value of measured peaks from each electrode (step 115) and comparing to a threshold ($S_5$ at step 117). In alternate embodiments other statistical parameters such as root mean square, absolute value, area under curve, and the like may be used. The results of the tests, e.g., comparing to respective thresholds, may result in an overall frailty score (step 118). Other results may also be employed, e.g., the values of the quantities measured, e.g., optionally normalized. By stratifying the score (step 119), assessment may be made as to whether the patient is frail, pre-frail, or non-frail.

In addition, frailty status may be identified by measuring the change in the response of EMG activation patterns to external loads, external cues (e.g., visual cue from flexion-extension, electrical stimulation, external force, and the like), and external distractions (e.g. cognitive distraction, dynamic distraction, and the like). The change in activation pattern may be assessed by changes in MFCV pattern, changes in EMG magnitudes, or delay of muscle activation with respect to external load, cue, or distraction.

Systems and methods according to present principles have been described which can objectively identify frailty using a simple and quick upper extremity motion. The calculations and determinations described may be performed locally, remotely by a server, or by a combination of client/server technologies. Predictions of frailty and pre-frailty were feasible with a high sensitivity and specificity when compared to the Fried Frailty Index. The systems and methods allow early identification of pre-frailty, e.g., for intervention with structured exercise, which has been demonstrated to slow or even reverse the progression of frailty. The systems and methods may be particularly useful for older adults in emergency, trauma or surgical settings who are unable to perform gait-based assessments, and may also be used as an outpatient tool for routine frailty assessment by low-cost paraprofessionals in a busy outpatient environment, where gait-based assessment is impractical.

Variations of systems and methods according to present principles will also be understood. For example, while flexion/extension of elbows and shoulders has been described above, it will be understood that flexion/extension may also be tested of a patient's knees, e.g., where sensors are disposed on a patient's upper leg, shin, and the like. In another variation, the system may include a group, collection or ensemble of sensors that may be placed on multiple locations on the body. These sensors may function individually, collectively, or with cross-talk. An array of sensors may be located on multiple locations on the body. Sensors may also be located within the body—either in a removable fashion or in an irremovable one.

The systems and methods according to current principles may be fully implemented in any number of computing devices. Typically, instructions are laid out on computer readable media, generally non-transitory, and these instructions are sufficient to allow a processor in the computing device to implement the method of the embodiments disclosed herein. The computer readable medium may be a hard drive or solid state storage having instructions that, when run, are loaded into random access memory. Inputs to the application, e.g., from the plurality of users or from any one user, may be by any number of appropriate computer input devices. For example, users may employ a keyboard, mouse, touchscreen, joystick, trackpad, other pointing device, or any other such computer input device to input data relevant to the calculations. Data may also be input by way of an inserted memory chip, hard drive, flash drives, flash memory, optical media, magnetic media, or any other type of file storing medium. The outputs may be delivered to a user by way of a video graphics card or integrated graphics chipset coupled to a display that maybe seen by a user.

Alternatively, a printer may be employed to output hard copies of the results. Given this teaching, any number of other tangible outputs will also be understood to be contemplated by the embodiments disclosed herein. For example, outputs may be stored on a memory chip, hard drive, flash drives, flash memory, optical media, magnetic media, or any other type of output. It should also be noted that the embodiments disclosed herein may be implemented on any number of different types of computing devices, e.g., personal computers, laptop computers, notebook computers, net book computers, handheld computers, personal digital assistants, mobile phones, smart phones, tablet computers, and also on devices specifically designed for these purposes. In one implementation, a user of a smart phone or Wi-Fi connected device downloads a copy of the application to their device from a server using a wireless Internet connection. An appropriate authentication procedure and secure transaction process may provide for payment to be made to the seller. The application may download over a mobile connection, or over Wi-Fi or other wireless network connection. Accelerometers and/or gyroscopes within the mobile device may be employed for the measurements. The application may then be run by the user. Such a networked system may provide a suitable computing environment for an implementation in which a plurality of users provides separate inputs to the system and method.

Computer System Embodiment

Figure 9:
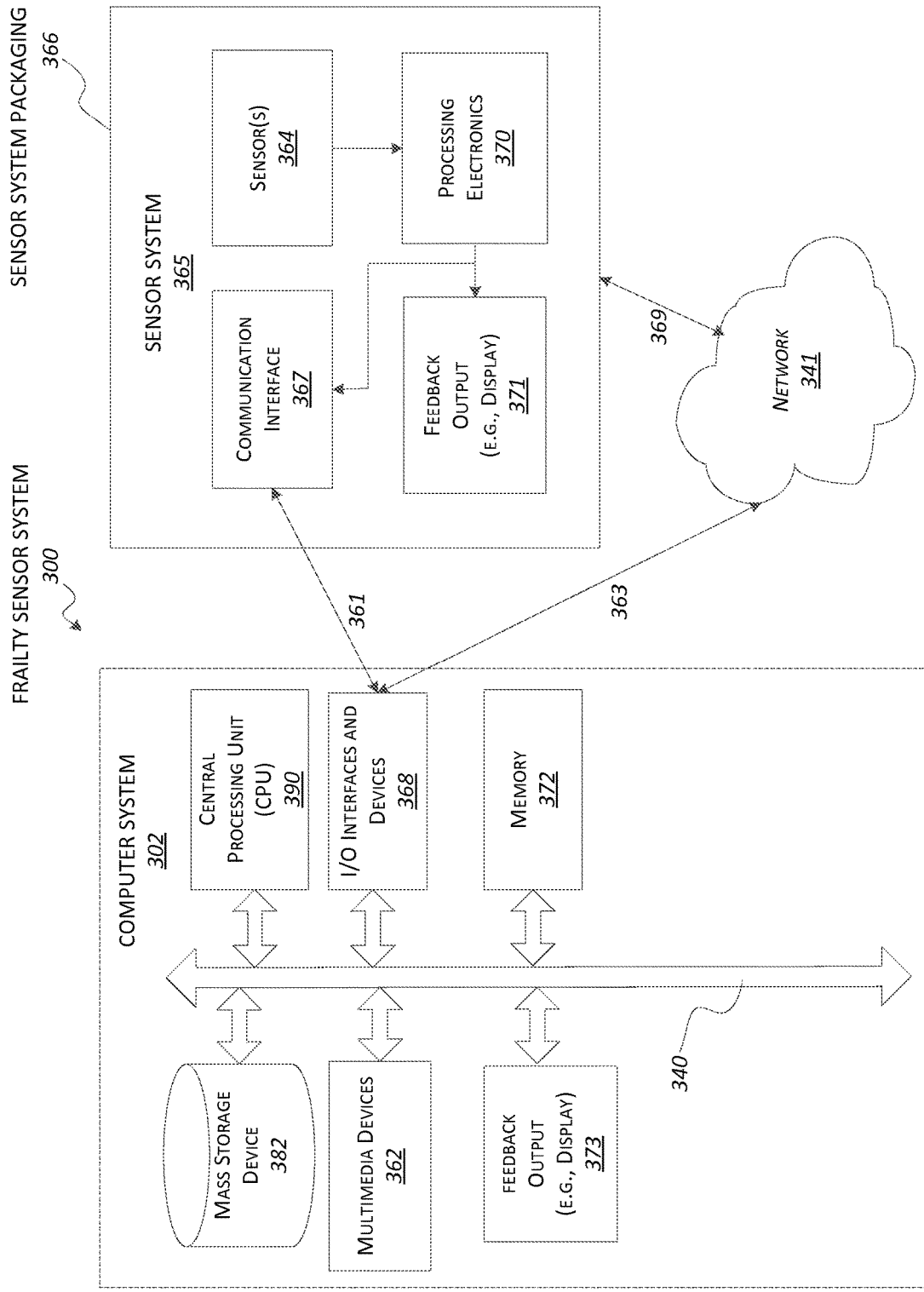
FIG. 9 is a block diagram illustrating an example embodiment of a frailty evaluation system in accordance with some embodiments.

FIG. 9 is a block diagram illustrating an example embodiment of a frailty sensor system 300 (e.g., frailty analysis and feedback system) in accordance with some embodiments. The system 300 can include a programmed computer system that comprises one or more computers or computing devices (e.g., wearable computers, smartphones or other mobile devices, laptop computers, application servers, database servers, workstations, storage servers, etc.) that execute code modules.

In some embodiments including the illustrated embodiment, the frailty sensor system 300 includes a computer system 302 and a sensor system 365 housed in a sensor system packaging 366. As indicated by the dashed box, the computer system 302 is optional and is not included in some embodiments, where the system 300 includes only the sensor system 365. In such cases, the sensor system 365 can implement some or all of the functionality described herein with respect to the computer system 302.

The packaging 366 of the sensor system 365 can be any appropriate type of packaging and can be adapted according to certain embodiments to attach to a portion of the patient's body above the waist, such as to the patient's shoulder, upper arm, elbow, forearm, wrist, hand, or fingers, or associated clothing, such as a sleeves, gloves, or the like. In some embodiments, the packaging 366 can be adapted to attach to a portion of the subject's body below the waist, such as a hip, upper leg, knee, shin, ankle, foot, or toes, or associated clothing, such as pants, shoes, or the like.

For instance, the packaging 366 can be similar to that shown with respect to the sensor 12 and/or sensor 14 of FIG. 1. The sensor system 365 can include, and in the illustrated embodiment does include, one or more body worn sensors 364, processing electronics 370, feedback output 371, and a communication interface 367.

The sensor(s) 364 can be any of the sensors described herein including inertial sensors (such as accelerometers and gyroscopes), and/or EMG sensors, and can also include other types of sensors including magnetometers. Depending on the embodiment, combinations of any of the foregoing sensor types can be used.

The processing electronics 370 can generally be configured to process the data received from the sensors 364, and may include digital logic circuitry. For instance, the processing electronics 370 can be implemented using one or more microprocessors, microcontrollers, field-programmable gate arrays (FPGAs), combinations of the same or the like. In some cases the processing electronics 364 can also include appropriate analog circuitry, e.g., front-end circuitry including analog-to-digital converters and associated componentry for processing signals received from the sensors 364.

The processing electronics 370 can include a microprocessor executing firmware or other programmable instructions configured to implement an algorithm (e.g., frailty analysis algorithm associated with the frailty information as described herein) for determining one or more characteristics associated with body segment movement (e.g., upper limbs as discussed herein) of a person wearing the sensors 364 and/or to provide feedback information related to the body segment movement (e.g., feedback information related to one or more frailty characteristics, variables, measurements, calculations, and/or the like as described herein). The processing electronics 370 can be designed to determine any of the frailty characteristics, variables, measurements, calculations, and/or the like described herein and/or provide information usable to generate any of the types of feedback described herein (e.g., visual, audible, tactile, etc.).

The feedback output 371 is in communication with the processing electronics 370 (and in some cases directly with the sensors 364), and can generally be configured to provide feedback to the user and/or clinician based on information received from the processing electronics 370 and/or other patient characteristics (e.g., anthropometric data). For instance, the feedback output can comprise a liquid crystal display or other type of display for providing graphical feedback, a touchscreen display, one or more light-emitting diodes or other visual indicators, a speaker for providing audible feedback, a vibration mechanism for providing tactile feedback, or any combination thereof. In some embodiments including some of those where the frailty system 300 includes a separate computer system 302, the sensor system 365 does not include the feedback output 371, and instead communicates feedback information to the computer system 302 which in turn outputs the biofeedback to the user and/or clinician. In some embodiments, the computer system 302 and the sensor system 365 are both capable of providing feedback and/or frailty information to the user and/or clinician.

The communication interface 367 can include a wireless transceiver or transmitter for delivering information to the computer system 302 over the communication link 361. The communication interface 367 can support any appropriate protocol (e.g., Bluetooth, Wi-Fi, etc.). In some cases, the sensor system 365 and the computer system 302 communicate over a wired link instead of a wireless link. In one embodiment, the computer system 302 is a smartphone that is connected to the sensor system 365 via Bluetooth or some other wireless or wired communication link.

The computer system 302 can comprise one or more mobile devices or personal computers, such as one or more mobile devices or computers that are Windows, Macintosh, Android, iOS, or Linux/Unix compatible. In some embodiments, the computer system 302 comprises one or more servers, desktop computers, laptop computers, personal digital assistants, kiosks, or mobile devices (e.g., smartphones), for example. The computer system 302 can include a display 389 to display feedback, and/or frailty information (e.g., frailty characteristics, variables, measurements, calculations, and/or the like as discussed herein), and/or other patient characteristics (e.g., anthropometric data). The exemplary computer system 302 includes a central processing unit ("CPU") 390, which may include one or more conventional microprocessors. The computer system 302 can further include memory 372, such as random access memory ("RAM") for temporary storage of information and a read only memory ("ROM") for permanent storage of information, and/or a mass storage device 382, such as a hard drive, diskette, solid-state drive, or optical media storage device. The mass storage device 382 may store data collected from a plurality of sensors or remotely collected sensor data, and/or calculated body segment parameter data from various trials. The components and modules of the computer system 302 can be connected using a bus system 340. In some embodiments, the bus system 340 is compatible with one or more of Peripheral Component Interconnect ("PCI"), Microchannel, Small Computer System Interface ("SCSI"), Industrial Standard Architecture ("ISA") and Extended ISA ("EISA") architectures, for example. In some embodiments, the functionality provided for in the components and modules of the frailty sensor system 300 may be combined into fewer components and modules or further separated into additional components and modules.

The computer system 302 can be controlled and coordinated by operating system software, such as Windows Server, Linux Server, Windows XP, Windows Vista, Windows 7, Unix, Linux, SunOS, Solaris, Android, iOS, or other compatible server, desktop, or mobile operating systems. In Macintosh systems, the operating system may be any available operating system, such as MAC OS X. In other embodiments, the computer system 300 may be controlled by a proprietary operating system. Conventional operating systems control and schedule computer processes for execution, perform memory management, provide file system, networking, I/O services, and provide a user interface, such as a graphical user interface ("GUI"), among other things.

The computer system 302 may include one or more commonly available input/output (I/O) devices and interfaces 368, such as a keyboard, mouse, touchpad, and printer. The I/O devices may also include the one or more sensors 364 worn on a user's body, as described above. In some embodiments, these devices may be linked physically to the system 302, or may be linked wirelessly via interfaces such as Bluetooth and/or Wi-Fi.

The computer system 302 can also include a feedback output 373, which can be separate from or form a part of the I/O devices and interfaces 368, and can include one or more display devices, such as a monitor, that allows the visual presentation of data to a user (e.g., the visual feedback user interface described above for providing visual feedback relating to body segment movement and/or frailty information). More particularly, a display device provides for the presentation of GUIs, application software data, and multimedia presentations, for example. The feedback output 373 can include one or more speakers and/or tactile output devices (e.g., vibration mechanisms) for providing audible and tactile biofeedback, respectively, relating to body segment movement and/or frailty information.

The frailty sensor system 300 may also include one or more multimedia devices 362, video cards, graphics accelerators, and microphones, for example. In some embodiments, such as when the frailty sensor system 300 comprises a network server, for example, the computing system may not include any of the above-noted man-machine I/O devices.

In some embodiments, the I/O devices and interfaces 368 provide a communication interface to various external devices. For example, the frailty sensor system 300 can electronically couple to the network 341, which may comprise one or more of a LAN, WAN, or the Internet, for example, via a wired, wireless, or combination of wired and wireless, communication link 363. The network 341 can facilitate communications among various computing devices and/or other electronic devices via wired or wireless communication links. The frailty sensor system 300 may use network 341 to receive sensor data collected remotely and transmit such resulting data back to the user. For example, a user may wear sensors 12, 14 during frailty test (e.g., physical test as described herein). The sensors 12, 14 may be configured to transmit data (through a wired or wireless connection) to a mobile computing device (e.g., a smartphone, a laptop computer, a tablet, etc.). The mobile computing device may in turn transmit the collected sensor data via the network 341 to the frailty sensor system 300, which may, as described above, process the received data and provide feedback data back to the mobile computing device. The feedback data may then be used by the mobile computing device to display a visual feedback to the user (e.g., via the user interface described above). In this manner, the user can receive near-instantaneous feedback of body segment movement. As shown, the sensor system 365 can also be in communication with the network 341. For instance, the sensor system 365 and the computer system 302 in some embodiments are in communication with one another via a WAN, LAN or other network 341 via the link 369 instead of communicating via the link 361.

As illustrated, in embodiments where a separate computer system 302 is used, the functionality of the frailty sensor system 300 can be distributed between the computer system 302 and the sensor system 365. For instance, in some embodiments, the sensor system 365 generally obtains sensor data relating to a person's body segment movement, processes the sensor data to identify characteristics associated with the quantity or type of the body segment movement, and/or generates information for providing feedback regarding the body segment movement, such as feedback regarding frailty. The computer system 302 receives the feedback information and outputs the information using the biofeedback output 373. One benefit of this configuration is that relatively less information may be sent between the sensor system 365 and the computer system 302 as compared to a situation where the computer system 302 processes the sensor data itself. For instance, the processing electronics 370 may generate relatively lightweight descriptors (e.g., 8-bit or 16-bit descriptors) or identifiers relating to certain identified body segment movement characteristics and/or types of feedback, which are forwarded to the computer system 302 via the communication interface 367.

The functionality of the frailty sensor system 300 can be distributed in other ways, depending on the embodiment. For example, in some cases, the processing electronics 370 is not included, or performs minimal processing on the data obtained from the sensor 364. The sensor data is forwarded to the computer system 302 which implements the algorithm for analyzing body segment movement, generating feedback information, and the like. In other cases, such as where the sensor system 365 includes the feedback output 371, the entire frailty sensor system 300 resides in the sensor system packaging 366, and a separate computer system 302 is not used.

In addition to the devices that are illustrated in, for example, FIG. 1, the frailty sensor system 300 may communicate with other data sources or other computing devices. For example, collected data may be stored in a local or remote database by the frailty sensor system 300, so that a user's performance can be tracked over time.

The frailty sensor system 300 may also include one or more software modules to process and/or perform the functionalities discussed herein, for example, the methods and processes in FIGS. 2 to 8. The software module may be stored in mass storage 382 and/or memory 372, and implemented as one or more modules, which may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Alternately, the software module may be implemented as separate devices, such as computer servers. In alternate embodiments, the frailty sensor system 300 can be implemented by multiple physical computers that are interconnected, with different functions or tasks optionally handled by different machines.

In general, the word "module," as used herein, refers to logic embodied in hardware or firmware, or to a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

Embodiments Incorporating Two or More Sensors

Figure 10:
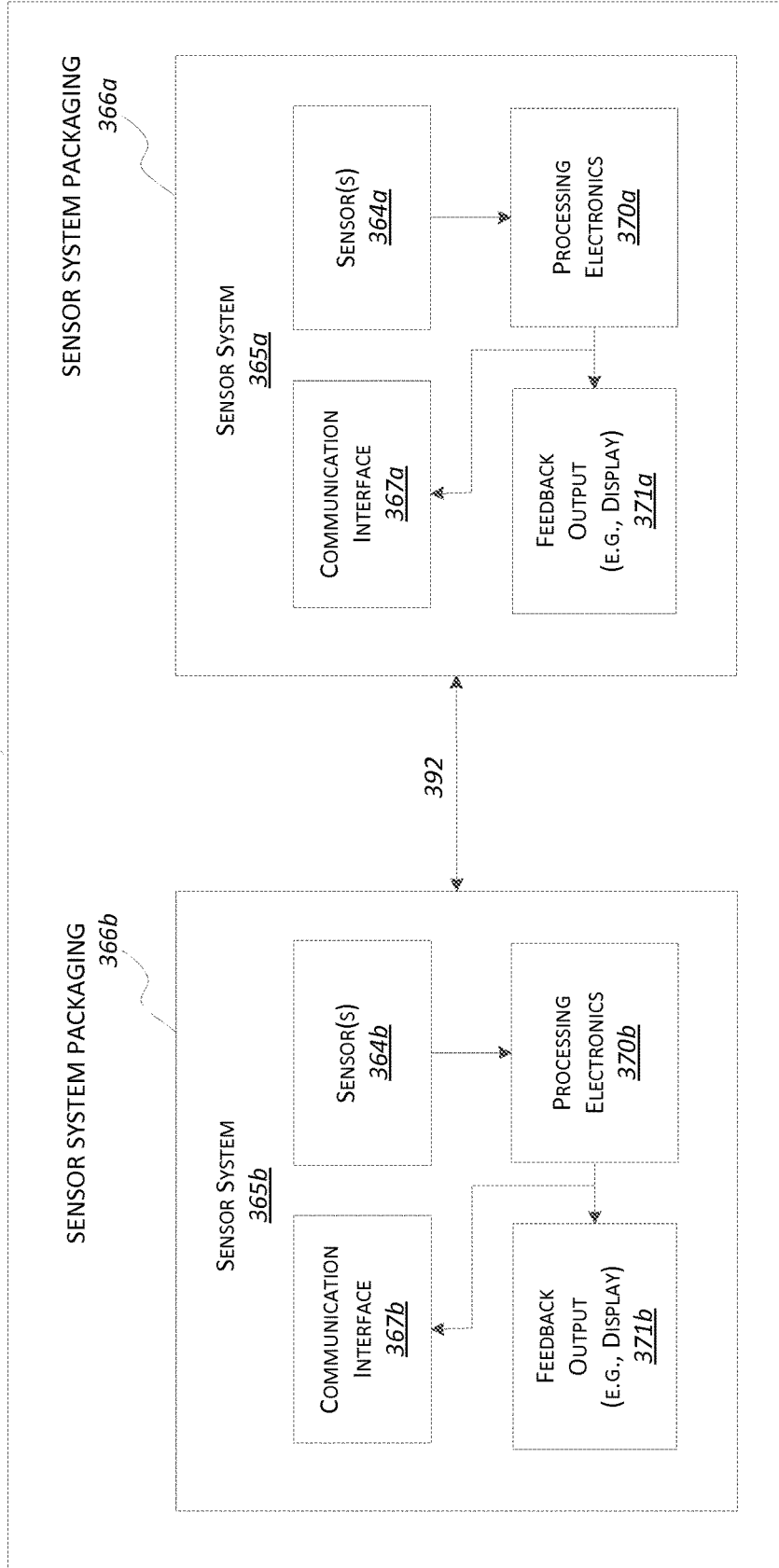
FIG. 10 is a block diagram illustrating an example embodiment of a frailty evaluation system including two movement sensors.

FIG. 10 is a block diagram illustrating an example embodiment of two sensors (e.g., sensor system 365*a* and sensor system 365*b*). In some embodiments, the sensor system 365*a* may be an inertial sensor as discussed herein, and the sensor system 365*b* may be an EMG sensor as discussed herein. In some embodiments, the frailty assessment systems and methods described herein may implement two or more sensor systems 365, including three, four, five, six, or more. Each sensor system 365*a*, 365*b* may be connected to an extremity (and/or other body portions of the patient as discussed herein) via an elastic band at desired or predetermined positions on, for example, the arm as discussed herein in reference to FIG. 1.

The sensor systems 365*a*, 365*b* may each have a varying combination of components discussed herein. For instance, the sensor systems 365*a*, 365*b* may each have one or more sensor(s) 364*a*, 364*b*, sensor system packaging 366*a*, 366*b*, communications interface 367*a*, 367*b*, processing electronics 370*a*, 370*b*, and/or feedback output 371*a*, 371*b*. For example, the sensor system 365*a* may have sensor(s) 364*a*, a sensor system packaging 366*a*, a communications interface 367*a*, processing electronics 370*a*, and feedback output 371*a*, while the sensor system 365*b* may have, for example, the sensor(s) 364*b* and the sensor system packaging 366*b*. Accordingly, the sensor system 365*b* may communicate sensor data to the sensor system 365*a* (via communication link 392) for the sensor system 365*a* to process the sensor data from the sensor system 365*b* (via processing electronics 367*a*) and provide feedback via the feedback output 371*a*. Frailty information as discussed herein provided on the feedback output 371*a* may be associated with one or both of the sensor systems 365*a*, 365*b*. In some embodiments, the sensor system 365*b* may include processing electronics 370*b* such that frailty information is communicated to the sensor system 365*a* ready to be displayed on the feedback output 371*a*.

The sensor systems 365*a*, 365*b* may communicate over a communication link 392. The communication link 392 can be electrical wire(s) connecting the sensor systems 365*a*, 365*b* (e.g., via the communication interfaces 367*a*, 367*b*). In some embodiments, the communication interfaces 367*a*, 367*b* may be wireless transceivers or transmitters to deliver information between the sensor systems 365*a*, 365*b*. The communication interfaces 367*a*, 367*b* may support any appropriate protocol (e.g., Bluetooth, Wi-Fi, etc.).

The two or more sensor systems 365*a*, 365*b* may be housed in or positioned on a sensor system housing 393. The sensor system housing 393 can be designed to position both sensor systems 365*a*, 365*b* in desired or predetermined positions on an extremity of a patient (and/or other body portions of the patient as discussed herein). For example, the sensor system housing 393 may be a substantially arm-length sleeve that a patient slips or positions over an arm. Once the sensor system housing 393 is properly positioned on the arm at a desired or predetermined position, the sensor systems 365*a*, 365*b* can be correspondingly positioned at their respective desired or predetermined positions on the arm (e.g., positions of the sensors 12, 14 as discussed herein in reference to FIG. 1).

List of Example Numbered Embodiments

The following is a list of example numbered embodiments. The features recited in the below list of example embodiments can be combined with additional features disclosed herein. Furthermore, additional inventive combinations of features are disclosed herein, which are not specifically recited in the below list of example embodiments and which do not include the same features as the specific embodiments listed below. For sake of brevity, the below list of example embodiments does not identify every inventive aspect of this disclosure. The below list of example embodiments are not intended to identify key features or essential features of any subject matter described herein.

1. A method for determining frailty of a person, the method comprising:
    receiving one or more signals generated by at least one movement sensor configured to measure the movement of a limb of a person;
    with processing electronics comprising digital logic circuitry, processing sensor data derived from the one or more signals of the at least one movement sensor to determine a first variable associated with movement of the limb of the person; and based at least in part on the first variable, generating information usable to determine frailty of the person.

2. The method of embodiment 1, wherein the first variable comprises at least one of a position of the limb, a joint angle associated with the limb, an angular velocity associated with movement of the limb, or an acceleration associated with movement of the limb.

3. The method of embodiment 1, wherein the processing results in a determination of values of the first variable associated with repeated movements of the limb over at least one of a predetermined period of time or a predetermined number of repetitions of movement.

4. The method of embodiment 3, wherein the predetermined period of time falls within a range of between about 10 seconds to about 60 seconds.

5. The method of embodiment 1, wherein the movement of the limb of the person comprises at least one of a flexing movement of the limb or an extension movement of the limb.

6. The method of embodiment 1, wherein the at least one movement sensor is a camera configured to measure the position of a limb of a person.

7. The method of embodiment 1, wherein the at least one movement sensor is supported at a position on a limb of a person.

8. The method of embodiment 7, wherein the limb of the person comprises an upper limb, and wherein the at least one movement sensor is attached to a forearm of the person.

9. The method of embodiment 7, wherein the at least one movement sensor comprises at least one of an accelerometer, a gyroscope, or a goniometer.

10. The method of embodiment 7, wherein the one or more signals of the at least one movement sensor are generated by at least first and second movement sensors, wherein the first movement sensor is attached to the forearm of the person, and the second movement sensor is attached to the upper arm of the person.

11. The method of embodiment 7, wherein the limb of the person is a lower limb, and wherein the at least one movement sensor is attached to a shin of the lower limb of the person.

12. The method of embodiment 1, wherein the movement of the limb is associated with movement at an elbow of the person, a knee of the person, or both the elbow and the knee of the person.

13. The method of embodiment 1, further comprising:
with the processing electronics, determining a second variable based at least in part on the first variable; and
based at least in part on the first variable and the second variable, generating information usable to determine frailty of the person.

14. The method of embodiment 12, wherein the first variable comprises angular velocity, and wherein the second variable comprises at least one of angular acceleration based at least in part on the angular velocity or angle based at least in part on the angular velocity.

15. The method of embodiment 12, further comprising:
receiving or determining, with the processing electronics, a third variable, wherein the third variable comprises anthropometric data of the person; and
based at least in part on the first variable, the second variable, and the third variable, generating information usable to determine frailty of the person.

16. The method of embodiment 1, wherein the generated information usable to determine frailty of the person comprises at least one measure determined by the processing electronics, wherein the at least one measure comprises at least one of speed of movement, reduction in speed of movement over a predetermined period of time, flexibility in movement, power of movement, rise time of movement, number of movements over the predetermined period of time, jerkiness of movement, or moment of movement.

17. The method of embodiment 16, further comprising, with the processing electronics, determining at least one frailty marker based at least in part on the at least one measure, wherein the at least one frailty marker comprises at least one of slowness, weakness, exhaustion, or flexibility.

18. The method of embodiment 17, further comprising, with the processing electronics, determining a frailty status associated with a person, the frailty status based at least in part on the at least one frailty marker, the frailty status comprising a non-frail status, a pre-frail status, and a frail status.

19. The method of embodiment 16, wherein the at least one measure of speed of movement is more indicative relative to other measures in determining whether the frailty status is the non-frail status or the pre-frail status.

20. The method of embodiment 16, wherein the at least one measure of power of movement is more indicative relative to other measures in determining whether the frailty status is the pre-frail status or the frail status.

21. The method of embodiment 1, further comprising:
receiving one or more signals generated by the at least one movement sensor corresponding to movement of another limb of the person; and
with the processing electronics, processing sensor data derived from the one or more signals corresponding to the movement of the other limb to determine the first variable associated with movement of the other limb of the person.

22. The method of embodiment 21, wherein the at least one movement sensor includes a first sensor that measures the movement of the limb of the person and that also measures the movement of the other limb of the person.

23. The method of embodiment 22, wherein the first sensor measures movement of the limb when supported on the limb and measures movement of the other limb when supported on the other limb.

24. The method of embodiment 21, wherein the at least one movement sensor includes first and second sensors, the first sensor measuring movement of the limb of the person and the second sensor measuring movement of the other limb of the person.

25. The method of embodiment 1, wherein the at least one movement sensor comprises a display configured to display at least one of a frailty score or a frailty status of the person based at least in part on the generated information.

26. The method of embodiment 1, further comprising wirelessly transmitting to a separate computer system the generated information usable to determine frailty of the person.

27. A method for determining frailty of a person, the method comprising:
receiving one or more signals generated by at least one electromyographic sensor supported at a position on the limb of a person;
with processing electronics comprising digital logic circuitry, processing sensor data derived from the one or more signals of the at least one electromyographic sensor to determine at least one of a muscle fiber conductive velocity or a muscle activation pattern, the muscle fiber conductive velocity and the muscle activation pattern associated with movement of the limb of the person; and based at least in part on at least one of the muscle fiber conductive velocity or the muscle activation pattern, generating information usable to determine frailty of the person.

28. The method of embodiment 27, wherein information generated based at least in part on the muscle fiber conductive velocity comprises at least one change in the muscle fiber conductive velocity determined by the processing electronics, the at least one change comprising at least one of a reduction in muscle fiber conductive velocity, a coefficient of variation of the muscle fiber conductive velocity, or a mean value of the muscle fiber conductive velocity.

29. The method of embodiment 28, wherein the processing electronics determining the muscle activation pattern comprises determining at least one of a coefficient of variation of electromyographic peaks or a mean value of electromyographic peaks.

30. A frailty determination system, the system comprising:

at least one movement sensor configured to generate one or more signals; and processing electronics in communication with the at least one movement sensor configured to measure the movement of a limb of a person and comprising digital logic circuitry, the processing electronics configured to:
process sensor data derived from the one or more signals according to a frailty analysis algorithm;
based at least in part on the results of the processing of the sensor data, determine a first variable associated with movement of the limb of the person; and
based at least in part on the first variable, generate information usable to determine frailty of the person.

31. The system of embodiment 30, wherein the first variable comprises at least one of a position of the limb, a joint angle associated with the limb, an angular velocity associated with movement of the limb, or an acceleration associated with movement of the limb.

32. The system of embodiment 30, wherein processing the sensor data is configured to result in a determination of values of the first variable associated with repeated movements of the limb over at least one of a predetermined period of time or a predetermined number of repetitions of movement.

33. The system of embodiment 32, wherein the predetermined period of time falls within a range of between about 10 seconds to about 60 seconds.

34. The system of embodiment 30, wherein the movement of the limb of the person comprises at least one of a flexing movement of the limb or an extension movement of the limb.

35. The system of embodiment 30, wherein the at least one movement sensor is a camera configured to measure the position of a limb of a person.

36. The system of embodiment 30, wherein the at least one movement sensor is supported at a position on a limb of a person.

37. The system of embodiment 36, wherein the at least one movement sensor comprises at least one of an accelerometer, a gyroscope, or a goniometer.

38. The system of embodiment 36, wherein the limb of the person comprises an upper limb, and wherein the at least one movement sensor is attached to a forearm of the person.

39. The system of embodiment 36, wherein the at least one movement sensor comprises at least first and second movement sensors, and wherein the first movement sensor is attached to the forearm of the person, and the second movement sensor is attached to the upper arm of the person.

40. The system of embodiment 36, wherein the limb of the person is a lower limb, and wherein the at least one inertial sensor is attached to a shin of the lower limb of the person.

41. The system of embodiment 30, wherein the movement of the limb is associated with movement at an elbow of the person, a knee of the person, or both the elbow and the knee of the person.

42. The system of embodiment 30, wherein the processing electronics are further configured to:

based at least in part on the results of the processing of the sensor data, determine a second variable based at least in part on the first variable; and based at least in part on the first variable and the second variable, generate information usable to determine frailty of the person.

43. The system of embodiment 42, wherein the first variable comprises angular velocity, and wherein the second variable comprises at least one of angular acceleration based at least in part on the angular velocity or angle based at least in part on the angular velocity.

44. The system of embodiment 42, wherein the processing electronics are further configured to:

receive or determine a third variable, wherein the third variable comprises anthropometric data of the person; and based at least in part on the first variable, the second variable, and the third variable, generate information usable to determine frailty of the person.

45. The system of embodiment 30, wherein the processing electronics processes the sensor data according to the frailty analysis algorithm by at least determining with the processing electronics at least one measure, wherein the at least one measure comprises at least one of speed of movement, reduction in speed of movement over a predetermined period of time, flexibility in movement, power of movement, rise time of movement, number of movements over the predetermined period of time, jerkiness of movement, or moment of movement.

46. The system of embodiment 45, wherein the processing electronics processes the sensor data according to the frailty analysis algorithm by at least determining with the processing electronics at least one frailty marker based at least in part on the at least one measure, wherein the at least one frailty marker comprises at least one of slowness, weakness, exhaustion, or flexibility.

47. The system of embodiment 46, wherein the processing electronics processes the sensor data according to the frailty analysis algorithm by at least determining with the processing electronics a frailty status associated with a person, the frailty status based at least in part on the at least one frailty marker, the frailty status comprising a non-frail status, a pre-frail status, and a frail status.

48. The system of embodiment 45, wherein the at least one measure of speed of movement is more indicative relative to other measures in determining whether the frailty status is the non-frail status or the pre-frail status.

49. The system of embodiment 45, wherein the at least one measure of power of movement is more indicative relative to other measures in determining whether the frailty status is the pre-frail status or the frail status.

50. The system of embodiment 30, wherein the processing electronics are further configured to:
 process sensor data, derived from the one or more signals according to the frailty analysis algorithm, corresponding to movement of another limb of the person; and
 based at least in part on the results of the processing of the sensor data, determine the first variable associated with movement of the other limb of the person; and
 based at least in part on the first variable, generate information usable to determine frailty of the person.

51. The system of embodiment 50, wherein the at least one movement sensor includes a first sensor configured to measure the movement of the limb and also configured to measure the movement of the other limb.

52. The system of embodiment 50, wherein the at least one movement sensor includes a first sensor and a second sensor, the first sensor configured to measure the movement of the limb and the second sensor configured to measure the movement of the other limb.

53. The system of embodiment 30, further comprising a display configured to display at least one of a frailty score or a frailty status of the person based at least in part on the generated information.

54. The system of embodiment 30, wherein the processing electronics are further configured to wirelessly transmit to a separate computer system the generated information usable to determine frailty of the person.

55. A frailty determination system, the system comprising:
 at least one electromyographic sensor configured to generate one or more signals, and
 processing electronics in communication with the at least one electromyographic sensor,
 wherein the processing electronics are further configured to:
 process sensor data derived from the one or more signals of the at least one electromyographic sensor according to a frailty analysis algorithm, wherein the sensor data of the at least one electromyographic sensor is collected while the electromyographic sensor is supported on the limb of the person; and
 based at least in part on the results of the processing of the sensor data of the at least one electromyographic sensor, determine at least one of a muscle fiber conductive velocity or a muscle activation pattern, the muscle fiber conductive velocity and the muscle activation pattern associated with movement of the limb of the person; and
 based at least in part on at least one of the muscle fiber conductive velocity or the muscle activation pattern, generate information usable to determine frailty of the person.

56. The system of embodiment 55, wherein the processing electronics processes the sensor data according to the frailty analysis algorithm by at least determining at least one change in the muscle fiber conductive velocity, the at least one change comprising at least one of a reduction in muscle fiber conductive velocity, a coefficient of variation of the muscle fiber conductive velocity, or a mean value of the muscle fiber conductive velocity.

57. The system of embodiment 56, wherein determining the muscle activation pattern comprises determining at least one of a coefficient of variation of electromyographic peaks or a mean value of electromyographic peaks.

58. Non-transitory computer storage that stores executable code that directs computer hardware to at least:
 process sensor data derived from one or more signals generated by at least one movement sensor according to a frailty analysis algorithm, wherein the frailty analysis algorithm is designed such that the sensor data is processed according to the frailty analysis algorithm using sensor data corresponding to the movement of a limb of a person;
 based at least in part on results of the processing of the sensor data, determine a first variable associated with movement of the limb of the person; and
 based at least in part on the first variable, generate information usable to determine frailty of the person.

59. The non-transitory computer storage of embodiment 58, wherein the first variable comprises at least one of a position of the limb, a joint angle associated with the limb, an angular velocity associated with movement of the limb, or an acceleration associated with movement of the limb.

60. The non-transitory computer storage of embodiment 58, wherein the movement of the limb of the person comprises at least one of a flexing movement of the limb or an extension movement of the limb.

61. The non-transitory computer storage of embodiment 58, wherein the limb of the person comprises an upper limb, and wherein the at least one movement sensor is attached to a forearm of the person.

62. The non-transitory computer storage of embodiment 58, wherein the at least one movement sensor comprises at least first and second movement sensors, and wherein the first movement sensor is attached to the forearm of the person, and the second movement sensor is attached to the upper arm of the person.

63. The non-transitory computer storage of embodiment 58, wherein the limb of the person is a lower limb, and wherein the at least one movement sensor is attached to a shin of the lower limb of the person.

64. The non-transitory computer storage of embodiment 58, wherein the movement of the limb is associated with movement at an elbow of the person, a knee of the person, or both the elbow and the knee of the person.

65. The non-transitory computer storage of embodiment 58, wherein processing the sensor data is configured to result in a determination of values of the first variable associated with repeated movements of the limb over at least one of a predetermined period of time or a predetermined number of movement repetitions.

66. The non-transitory computer storage of embodiment 65, wherein the predetermined period of time falls within a range of between about 10 seconds to about 60 seconds.

67. The non-transitory computer storage of embodiment 58, wherein the computer hardware is further directed to at least:
 based at least in part on the results of the processing of the sensor data, determine a second variable based at least in part on the first variable; and
 based at least in part on the first variable and the second variable, generate information usable to determine frailty of the person.

68. The non-transitory computer storage of embodiment 67, wherein the first variable comprises angular velocity, and wherein the second variable comprises at least one of angular acceleration based at least in part on the angular velocity or angle based at least in part on the angular velocity.

69. The non-transitory computer storage of embodiment 67, wherein the computer hardware is further directed to at least:
receive or determine a third variable, wherein the third variable comprises anthropometric data of the person; and
based at least in part on the first variable, the second variable, and the third variable, generate information usable to determine frailty of the person.

70. The non-transitory computer storage of embodiment 58, wherein the computer hardware is further directed to at least determine at least one measure, wherein the at least one measure comprises at least one of speed of movement, reduction in speed of movement over a predetermined period of time, flexibility in movement, power of movement, rise time of movement, number of movements over the predetermined period of time, jerkiness of movement, or moment of movement.

71. The non-transitory computer storage of embodiment 70, wherein the computer hardware is further directed to at least determine at least one frailty marker based at least in part on the at least one measure, wherein the at least one frailty marker comprises at least one of slowness, weakness, exhaustion, or flexibility.

72. The non-transitory computer storage of embodiment 71, wherein the computer hardware is further directed to at least determine a frailty status associated with a person, the frailty status based at least in part on the at least one frailty marker, the frailty status comprising a non-frail status, a pre-frail status, and a frail status.

73. The non-transitory computer storage of embodiment 70, wherein the frailty analysis algorithm is designed such that the at least one measure of speed of movement is more indicative relative to other measures in determining whether the frailty status is the non-frail status or the pre-frail status.

74. The non-transitory computer storage of embodiment 70, wherein the frailty analysis algorithm is designed such that the at least one measure of power of movement is more indicative relative to other measures in determining whether the frailty status is the pre-frail status or the frail status.

75. The non-transitory computer storage of embodiment 58, wherein the frailty analysis algorithm is designed such that the sensor data is processed according to the frailty analysis algorithm using sensor data corresponding to the movement of another limb of the person, and wherein the computer hardware is further directed to at least:
based at least in part on the results of the processing of the sensor data corresponding to the movement of the other limb of the person, determine the first variable associated with movement of the other limb of the person; and
based at least in part on the first variable, generate information usable to determine frailty of the person.

76. The non-transitory computer storage of embodiment 58, wherein the at least one movement sensor comprises at least one of a gyroscope, an accelerometer, a goniometer, or a camera.

77. The non-transitory computer storage of embodiment 58, wherein the computer hardware is directed to at least display at least one of a frailty score or a frailty status of the person based at least in part on the generated information.

78. The non-transitory computer storage of embodiment 58, wherein the computer hardware is further directed to wirelessly transmit to a separate computer system at least the generated information usable to determine frailty of the person.

79. Non-transitory computer storage that stores executable code that directs computer hardware to at least:
process sensor data derived from one or more signals of at least one electromyographic sensor according to the frailty analysis algorithm, wherein the frailty analysis algorithm is designed such that the sensor data of at least one electromyographic sensor is processed according to the frailty analysis algorithm using sensor data obtained when the at least one electromyographic sensor is supported on the limb of the person; and
based at least in part on the results of the processing of the sensor data of the at least one electromyographic sensor, determine at least one of a muscle fiber conductive velocity or a muscle activation pattern, the muscle fiber conductive velocity and the muscle activation pattern associated with movement of the limb of the person; and
based at least in part on at least one of the muscle fiber conductive velocity or the muscle activation pattern, generate information usable to determine frailty of the person.

80. The non-transitory computer storage of embodiment 79, wherein the computer hardware is further directed to at least determine at least one change in the muscle fiber conductive velocity, the at least one change comprising at least one of a reduction in muscle fiber conductive velocity, a coefficient of variation of the muscle fiber conductive velocity, or a mean value of the muscle fiber conductive velocity.

81. The non-transitory computer storage of embodiment 79, wherein the computer hardware is further directed to at least determine the muscle activation pattern by determining at least one of a coefficient of variation of electromyographic peaks or a mean value of electromyographic peaks.

82. A method for determining frailty of a person, the method comprising:
receiving one or more signals generated by at least one sensor supported at a position on a body part of the person above the waist, the signals generated in response to repetitive movement of the body part;
with processing electronics comprising digital logic circuitry, processing sensor data derived from the one or more signals of the at least one sensor to generate information usable to determine frailty of the person; and
based on the information, generating display data usable to display information relating to the frailty of the person on an electronic display.

83. A frailty determination system, the system comprising:
at least one sensor adapted for attachment to a body part of a person above the waist and configured to generate one or more signals in response to movement of the body part; and
processing electronics in communication with the at least one sensor and comprising digital logic circuitry, the processing electronics configured to:
process sensor data derived from the one or more signals according to a frailty analysis algorithm, wherein the sensor data is collected while the sensor is attached to the body part; and
based at least in part on results of the processing of the sensor data according to the frailty analysis algorithm, generate display data usable to display information relating to the frailty of the person on an electronic display.

84. A method for diagnosing frailty, comprising:
sensing a first variable relating to frailty in a patient;
calculating a second variable from the first variable;
determining or receiving a third variable relating to frailty in the patient;
using the first, second, and third variables to determine at least one marker relating to frailty; and
classifying the patient as non-frail, pre-frail, or frail according to the marker.

85. The method of embodiment 84, wherein the sensing is performed by a gyroscope. 86. The method of embodiment 85, wherein the gyroscope is within a device attached to an extremity of the patient.

87. The method of embodiment 84, further comprising displaying an output of the classification.

88. The method of embodiment 86, wherein the displaying is performed on the device.

89. The method of embodiment 86, wherein the displaying is performed on a remote device in signal communication with the device attached to an extremity of the patient.

90. The method of embodiment 89, wherein the remote device is a mobile device.

91. The method of embodiment 89, wherein the remote device is a tablet, a laptop, or a desktop computer.

92. The method of embodiment 84, wherein the extremity is an upper arm, a forearm, an upper leg, a shin, or a head.

93. The method of embodiment 84, wherein two sensors are provided, and the sensors are attached to an upper arm and a forearm.

94. The method of embodiment 84, wherein the sensing is performed by a motion capture system.

95. The method of embodiment 84, wherein the sensing is performed by a goniometer.

96. The method of embodiment 84, wherein the sensing is performed by an accelerometer.

97. The method of embodiment 84, wherein the first variable is angular velocity.

98. The method of embodiment 97, wherein the second variable is angle or angular acceleration.

99. The method of embodiment 84, wherein the first variable is joint angle.

100. The method of embodiment 99, wherein the second variable is angular velocity or angular acceleration.

101. The method of embodiment 84, wherein the first variable is angular acceleration.

102. The method of embodiment 101, wherein the second variable is angle or angular velocity.

103. The method of embodiment 84, wherein the third variable includes anthropometric data of the patient.

104. The method of embodiment 84, wherein the second variable is calculated from sensor data associated with the first variable.

105. The method of embodiment 84, wherein the third variable is not calculated.

106. The method of embodiment 84, wherein the determining a third variable includes receiving user input about the third variable.

107. The method of embodiment 84, wherein the first, second, and third variables are used to determine at least one marker relating to frailty, where the at least one marker is at least one of slowness, weakness, and exhaustion.

108. The method of embodiment 107, wherein the first, second, and third variables are used to determine a fourth marker relating to frailty, the fourth marker being related to flexibility.

109. The method of embodiment 107, wherein the first, second, and third variables are used to determine a variable of speed and a variable of rise time, and wherein the determined variables of speed and risetime are used to determine the marker of slowness.

110. The method of embodiment 107, wherein the first, second, and third variables are used to determine a variable of power and a variable of moment, and wherein the determined variables of power and moment are used to determine the marker of weakness.

111. The method of embodiment 107, wherein the first, second, and third variables are used to determine a variable of speed reduction and a variable of jerkiness, and wherein the determined variables of speed reduction and jerkiness are used to determine the marker of exhaustion.

112. A non-transitory computer readable medium, comprising instructions for causing a computing environment to perform the method of embodiment 84.

113. A method for diagnosing frailty, comprising:
sensing a first variable relating to frailty in a patient;
using the first variable to determine at least one marker relating to frailty; and
classifying the patient as non-frail, pre-frail, or frail according to the marker.

114. The method of embodiment 113, further comprising calculating a second variable from the first variable, and wherein the using further comprises using the first and second variables to determine the at least one marker relating to frailty.

115. The method of embodiment 114, further comprising determining or receiving a third variable relating to frailty in the patient, and wherein the using further comprises using the first, second, and third variables to determine at least one marker relating to frailty.

116. A method for diagnosing frailty, comprising:
placing a plurality of EMG sensors on at least one limb of a patient, separated by a common predetermined distance;
in response to patient activity, measuring muscle fiber conductive velocity;
measuring a change in a variable relating to muscle fiber conductive velocity during an interval in which the patient activity occurs; and
correlating the change in the variable to frailty.

117. The method of embodiment 116, wherein the variable is a reduction in muscle fiber conductive velocity across multiple flexion cycles, a coefficient of variation of measured muscle fiber conductive velocity during consecutive flexion cycles, or a mean value of measured muscle fiber conductive velocity during consecutive flexion cycles, or a combination of the above.

118. The method of embodiment 116, wherein the correlating includes measuring a muscle activation pattern during a maximum voluntary contraction protocol, and assessing the muscle activation pattern across multiple EMG electrodes.

119. The method of embodiment 118, wherein the assessing includes measuring the coefficient of variation of EMG peaks measured by electrodes or a mean value of measured peaks from each electrode.

120. The method of embodiment 116, wherein the correlating includes measuring a change in response of EMG activation pattern to external load, external cue, and/or external distraction.

121. The method of embodiment 120, wherein the measuring includes determining a change in a muscle fiber conductive velocity pattern, a change in an EMG magnitude, or a delay of a muscle activation with respect to an external load, use, or distraction.

122. A non-transitory computer readable medium comprising instructions for causing a computing environment to perform any of the above methods.

123. A system to perform any of the above methods.

124. A system for identifying frailty, comprising:
   a sensor;
   a computing environment to analyze signals received from the sensor, the computing environment including a non-transitory computer readable medium comprising instructions for causing a computing environment to perform the following steps:
      sensing a first variable relating to frailty in a patient;
      determining or receiving a second variable relating to frailty in the patient;
      using the first and second variables to determine at least one marker relating to frailty; and
      classifying the patient as non-frail, pre-frail, or frail according to the marker.

125. The system of embodiment 124, further comprising determining or calculating a third variable, and using the first, second, and third variables to determine the at least one marker.

126. The system of embodiment 124, wherein the sensor includes an accelerometer.

127. The system of embodiment 124, wherein the sensor includes a gyroscope.

128. The system of embodiment 124, wherein the sensor is configured to measure muscle fiber conductive velocity.

Terminology

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the inventions are susceptible to various modifications, and alternative forms, specific examples thereof have been shown in the drawings and are herein described in detail. It should be understood, however, that the inventions are not to be limited to the particular forms or methods disclosed, but to the contrary, the inventions are to cover all modifications, equivalents, and alternatives falling within the spirit and scope of the various embodiments described and the appended claims. Any methods disclosed herein need not be performed in the order recited. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers, and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount. Features of embodiments disclosed herein preceded by a term such as "approximately", "about", and "substantially" as used herein represent the feature with some variability that still performs a desired function or achieves a desired result for that feature.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced embodiment recitation is intended, such an intent will be explicitly recited in the embodiment, and in the absence of such recitation no such intent is present. For example, as an aid to understanding, the disclosure may contain usage of the introductory phrases "at least one" and "one or more" to introduce embodiment recitations. However, the use of such phrases should not be construed to imply that the introduction of an embodiment recitation by the indefinite articles "a" or "an" limits any particular embodiment containing such introduced embodiment recitation to embodiments containing only one such recitation, even when the same embodiment includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce embodiment recitations. In addition, even if a specific number of an introduced embodiment recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, embodiments, or drawings, should be understood to contemplate the possibilities of including one of the terms, either of the terms, or both terms. For example, the phrase "A or B" will be understood to include the possibilities of "A" or "B" or "A and B."

Although the present subject matter has been described herein in terms of certain embodiments, and certain exemplary methods, it is to be understood that the scope of the subject matter is not to be limited thereby. Instead, the Applicant intends that variations on the methods and materials disclosed herein which are apparent to those of skill in the art will fall within the scope of the disclosed subject matter.

REFERENCES

[1] Polanczyk C A, Marcantonio E, Goldman L et al. Impact of age on perioperative complications and length of stay in patients undergoing noncardiac surgery. *Ann Intern Med* 2001; 134:637-643.
[2] Makary M A, Segev D L, Pronovost P J et al. Frailty as a predictor of surgical outcomes in older patients. *J Am Coll Surg* 2010; 210:901-908.
[3] Davenport D L, Bowe E A, Henderson W G et al. National Surgical Quality Improvement Program (NSQIP) risk factors can be used to validate American Society of Anesthesiologists Physical Status classification (ASA PS) levels. *Ann Surg* 2006; 243:636-644.
[4] Fried L P, Tangen C M, Walston J et al. Frailty in older adults: Evidence for a phenotype. *J Gerontol A Biol Sci Med Sci* 2001; 56A:M146-M156.
[5] Rockwood K, Andrew M, Mitnitski A. A comparison of two approaches to measuring frailty in elderly people. *J Gerontol A Biol Sci Med Sci* 2007; 62A:738-743.
[6] Rockwood K, Song X, MacKnight C et al. A global clinical measure of fitness and frailty in elderly people. *Can Med Assoc J* 2005; 173:489-495.
[7] Toosizadeh N, Mohler J, Najafi B. Assessing Upper Extremity Motion: An Innovative Method to Identify Frailty. *JGS* 2015; Manuscript No. 13451.
[8] Kubicki A, Bonnetblanc F, Petrement G, Ballay Y, Mourey F. Delayed postural control during self-generated perturbations in the frail older adults. *Clin Interv Aging*. 2012; 7: 65-75.
[9] Folstein M F, Folstein S E, McHugh P R. 'Mini-mental state'. A practical method for grading the cognitive state of patients for the clinician. *J Psychiatr Res* 1975; 12:189-198.

What is claimed is:

1. An improved method for determining and stratifying a frailty index of a person into categories or onto a continuous scale, the method comprising:
generating one or more movement signals by at least one movement sensor, the at least one movement sensor being configured to measure movement of a limb of the person;
determining a first variable associated with the movement of the limb of the person based on the one or more movement signals generated by the at least one movement sensor, the at least one movement sensor being a multi axial inertial sensor configured to measure or determine angular velocity of a limb about a joint, the determining including implementing an algorithm for analyzing body segment movement using signals from the at least one movement sensor, the algorithm further determining other variables associated with limb movement using differentiation or integration or both; and
determining the frailty index of the person based at least on the first variable and the determined other variables, wherein the first variable comprises a joint angular velocity associated with the movement of the limb over a predefined interval of time, the determining the frailty index comprising:
deriving a joint angular acceleration and a joint angular flexion angle from the joint angular velocity;
determining a flexibility score from the joint angular flexion angle over the predefined interval of time, the flexibility score reflecting a frailty phenotype of flexibility;
determining a speed score or a rise time score from the joint angular velocity over the predefined interval of time, the speed score or rise time score reflecting a frailty phenotype of slowness;
determining a speed reduction score or a jerkiness score from the joint angular velocity over the predefined interval of time, the speed reduction score or jerkiness score reflecting a frailty phenotype of exhaustion;
determining a power score or a moment score from the joint angular velocity and the joint angular acceleration, the power score or moment score reflecting a frailty phenotype of weakness; and
determining the frailty index of the person based on at least on a combination of the determined scores reflecting the frailty phenotypes of flexibility, slowness, exhaustion, and weakness,
and displaying an indication of the determined frailty index.

2. The method of claim 1, wherein the first variable further comprises at least one of a position of the limb, a joint angle associated with the limb, and an acceleration associated with the movement of the limb.

3. The method of claim 1, wherein the first variable is determined based on repeated movements of the limb over a predetermined period of time or based on a predetermined number of repetitions of the movement.

4. The method of claim 1, wherein the at least one movement sensor comprises a camera.

5. The method of claim 1, wherein the at least one movement sensor is attached to the limb of the person.

6. The method of claim 5, wherein the at least one movement sensor is at least one of an accelerometer, a gyroscope, or a goniometer.

7. The method of claim 5, wherein
the one or more movement signals of the at least one movement sensor are generated by a first movement sensor and a second movement sensor, and
the first movement sensor is attached to the forearm of the person, and the second movement sensor is attached to the upper arm of the person.

8. The method of claim 1, further comprising:
receiving or determining anthropometric data of the person, wherein
the determining the frailty index of the person based at least on the first variable further comprises determining the frailty index of the person based on the anthropometric data of the person.

9. The method of claim 1, further comprising:
determining a frailty status associated with the person based on the frailty index,
wherein the frailty status comprises a non-frail status, a pre-frail status, and a frail status.

10. The method of claim 1, further comprising:
generating one or more second movement signals generated by the at least one second movement sensor, the at least one second movement sensor being configured to measure movement of another limb of the person; and
processing second sensor data derived from the one or more second movement signals generated by the at least one second movement sensor to determine a second variable associated with the movement of the other limb of the person.

11. The method of claim 1, further comprising wirelessly transmitting the frailty index to a computer system.

12. The method of claim 1, wherein in determining the at least one frailty marker, the slowness is determined based on speed and rise time of the movement.

13. The method of claim 12, wherein
the speed of the movement is calculated as mean value of a range of the angular velocity for each flexion/extension repetition of repeated flexions/extensions performed during a predetermined amount of time, and
the rise time is calculated as mean value of time required to reach a maximum angular velocity for each of the flexion/extension repetition of the repeated flexions/extensions performed during the predetermined amount of time.

14. The method of claim 1, wherein in determining the at least one frailty marker, the weakness is determined based on power and moment of the movement.

15. The method of claim 14, wherein the power is calculated by deriving an angular acceleration, determining a range for the angular acceleration and a range for the angular velocity for each flexion/extension repetition of repeated flexion/extension performed during a predetermined amount of time, and then calculating a mean value of the range for the angular acceleration and the range for the angular velocity, and
the moment is estimated from a moment of inertia, the angular velocity, and the angular acceleration as a mean value of the maximum moment for each flexion/extension repetition of the repeated flexion/extension performed during the predetermined amount of time.

16. The method of claim 1, wherein in determining the at least one frailty marker, the exhaustion is determined based on speed reduction and jerkiness of the movement.

17. The method of claim 16, wherein the speed reduction is calculated as a difference in a range of the angular velocity between a first set of elbow flexions and a second set of elbow flexions as a percentage of initial range of the angular velocity, and
the jerkiness is calculated as a coefficient of variation of a rang of the angular velocity for each flexion/extension repetition of repeated flexion/extension performed during a predetermined amount of time.

18. The method of claim 1, wherein in determining the at least one frailty marker, the flexibility is determined based on magnitude of joint motion of the movement.

19. The method of claim 18, wherein
the magnitude of the joint motion of the movement is calculated as a mean value of a range of elbow flexion angle over consecutive flexion/extension repetitions.

20. A method for determining frailty of a person, the method comprising:
generating one or more movement signals by at least one movement sensor, the at least one movement sensor being configured to measure movement of at least one limb of the person and to identify a plurality of flexion cycles corresponding to the movement of the at least one limb of the person, the at least one movement sensor being a multi axial inertial sensor configured to measure or determine angular velocity of a limb about a joint, the determining including implementing an algorithm for analyzing body segment movement using signals from the at least one movement sensor;

generating two or more electromyographic signals by at least two electromyographic sensors attached to the limb of the person;

determining a muscle fiber conductive velocity during at least one of the plurality of flexion cycles identified by the at least one movement sensor based on sensor data derived from the two or more electromyographic signals generated by the at least two electromyographic sensors, the muscle fiber conductive velocity being associated with the at least one of the plurality of flexion cycles identified by the at least one movement sensor corresponding to the movement of the limb of the person; and determining the frailty of the person based on a change in the muscle fiber conductive velocity determined during the at least one of the plurality of flexion cycles identified by the at least one movement sensor, the change in the muscle fiber conductive velocity comprising a reduction in muscle fiber conductive velocity, a coefficient of variation of the muscle fiber conductive velocity, or a mean value of the muscle fiber conductive velocity, wherein the muscle fiber conductive velocity corresponding to the at least one of the plurality of flexion cycles is calculated by dividing an inter-electrode distance between the at least two electromyographic sensors by a time difference between two peaks of the two or more electromyographic signals generated by the at least two electromyographic sensors.

21. The method of claim 20, wherein
determining the frailty of the person further comprises determining muscle activation pattern, and
determining the muscle activation pattern comprises determining a coefficient of variation of electromyographic peaks and a mean value of electromyographic peaks.

22. An improved system for determining and stratifying a frailty index of a person into categories or onto a continuous scale, the system comprising:
at least one movement sensor configured to generate one or more movement signals based on at least one movement of a limb of a person; and
a processor, in conjunction with a memory, configured to receive one or more signals generated from the at least one movement sensor, determine a first variable associated with the movement of the limb of the person based on the one or more movement signals generated by the at least one movement sensor, the at least one movement sensor being a multi axial inertial sensor configured to measure or determine angular velocity of a limb about a joint, the determining including implementing an algorithm for analyzing body segment movement using signals from the at least one movement sensor, the algorithm further determining other variables associated with limb movement using differentiation or integration or both, and determine the frailty index of the person based at least on the first variable and the determined other variables, wherein
the first variable comprises a joint angular velocity associated with the movement of the limb over a predefined interval of time,
the processor determines the frailty of the person by:
deriving a joint angular acceleration and a joint angular flexion angle from the joint angular velocity;
determining a flexibility score from the joint angular flexion angle over the predefined interval of time, the flexibility score reflecting a frailty phenotype of flexibility;
determining a speed score or a rise time score from the joint angular velocity over the predefined interval of time, the speed score or rise time score reflecting a frailty phenotype of slowness;
determining a speed reduction score or a jerkiness score from the joint angular velocity over the predefined interval of time, the speed reduction score or jerkiness score reflecting a frailty phenotype of exhaustion;
determining a power score or a moment score from the joint angular velocity and the joint angular acceleration, the power score or moment score reflecting a frailty phenotype of weakness; and
determining the frailty index of the person based on at least on a combination of the determined scores reflecting the frailty phenotypes of flexibility, slowness, exhaustion, and weakness, and displaying an indication of the determined frailty index.

23. The system of claim 22, wherein the first variable further comprises at least one of a position of the limb, a joint angle associated with the limb, and an acceleration associated with the movement of the limb.

24. The system of claim 22, wherein the first variable is determined based on repeated movements of the limb over a predetermined period of time or a predetermined number of repetitions of the movement.

25. The system of claim 22, wherein the at least one movement sensor is a camera.

26. The system of claim 22, wherein the at least one movement sensor is attached to the limb of a person.

27. The system of claim 26, wherein the at least one movement sensor is at least one of an accelerometer, a gyroscope, or a goniometer.

28. The system of claim 26, wherein
the at least one movement sensor comprises at least a first movement sensor and a second movement sensor, and
the first movement sensor is attached to the forearm of the person, and the second movement sensor is attached to the upper arm of the person.

29. The system of claim 22, wherein the processor is further configured to:
receive or determine anthropometric data of the person, and
determine the frailty of the person further based on the anthropometric data of the person.

30. The system of claim 22, wherein the processor is configured to determine the at least one frailty marker comprising slowness, weakness, exhaustion, or flexibility based on speed of the movement, reduction in speed of the movement over a predetermined period of time, flexibility in the movement, power of the movement, rise time of the movement, number of the movements over the predetermined period of time, jerkiness of the movement, and moment of the movement.

31. The system of claim 22, wherein the processor determines the at least one frailty marker by determining:
the slowness based on speed and rise time of the movement,
the weakness based on power and moment of the movement,
the exhaustion based on speed reduction and jerkiness of the movement, and
the flexibility based on magnitude of joint motion of the movement.

32. The system of claim 31, wherein
the processor determines a frailty status associated with the person based on the at least one frailty marker, and
the frailty status comprises a non-frail status, a pre-fail status, and a frail status.

33. The system of claim 32, further comprising a display configured to display at least one of a frailty score or a frailty status of the person based at least on the generated information.

34. The system of claim 22, wherein the processor is further configured to wirelessly transmit the at least one frailty marker to a separate computer system.

35. A frailty determination system, the system comprising:
at least one movement sensor configured to generate one or more movement signals, the at least one movement sensor being configured to measure movement of at least one limb of a person and to identify a plurality of flexion cycles corresponding to the movement of the at least one limb of the person, the at least one movement sensor being a multi axial inertial sensor configured to measure or determine angular velocity of a limb about a joint, the determining including implementing an algorithm for analyzing body segment movement using signals from the at least one movement sensor;
at least two electromyographic sensors attached to the person and configured to generate two or more electromyographic signals; and
a processor, in conjunction with a memory, configured to determine a muscle fiber conductive velocity during at least one of the plurality of flexion cycles identified by the at least one movement sensor based on sensor data derived from the two or more electromyographic signals generated by the at least two electromyographic sensor, the muscle fiber conductive velocity being associated with the at least one of the plurality of flexion cycles identified by the at least one movement sensor corresponding to the movement of the limb of the person, and determine the frailty of the person based on a change in the muscle fiber conductive velocity determined during the at least one of the plurality of flexion cycles identified by the at least one movement sensor, the change in the muscle fiber conductive velocity comprising a reduction in muscle fiber conductive velocity, a coefficient of variation of the muscle fiber conductive velocity, or a mean value of the muscle fiber conductive velocity,
wherein the muscle fiber conductive velocity corresponding to the at least one of the plurality of flexion cycles is calculated by dividing an inter-electrode distance between the at least two electromyographic sensors by a time difference between two peaks of the two or more electromyographic signals generated by the at least two electromyographic sensors.

36. The system of claim 35, wherein
the processor determines the frailty of the person based on a change in the muscle fiber conductive velocity, and the change in the muscle fiber conductive velocity comprises a reduction in muscle fiber conductive velocity, a coefficient of variation of the muscle fiber conductive velocity, and a mean value of the muscle fiber conductive velocity.

37. The system of claim 35, wherein
the processor the frailty of the person by further determining a muscle activation pattern, and
the processor determines the muscle activation pattern by determining a coefficient of variation of electromyographic peaks and a mean value of electromyographic peaks.

38. Non-transitory computer storage that stores executable code that directs computer hardware to:
receive one or more movement signals generated by at least one movement sensor, the at least one movement sensor being configured to measure joint rotational movement of a limb of a person;
determine a first variable associated with the movement of the limb of the person based on one or more movement signals generated by at least one movement sensor, the at least one movement sensor being a multi axial inertial sensor configured to measure or determine angular velocity of a limb about a joint, the determining including implementing an algorithm for analyzing body segment movement using signals from the at least one movement sensor, the algorithm further determining other variables associated with limb movement using differentiation or integration or both; and
determine a frailty of the person based at least on the first variable and the determined other variables, wherein
the first variable comprises a joint angular velocity associated with the movement of the limb over a predefined interval of time,
the determining the frailty of the person based at least on the first variable includes:
deriving a joint angular acceleration and a joint angular flexion angle from the joint angular velocity;
determining a flexibility score from the joint angular flexion angle over the predefined interval of time, the flexibility score reflecting a frailty phenotype of flexibility;
determining a speed score or a rise time score from the joint angular velocity over the predefined interval of time, the speed score or rise time score reflecting a frailty phenotype of slowness;
determining a speed reduction score or a jerkiness score from the joint angular velocity over the predefined interval of time, the speed reduction score or jerkiness score reflecting a frailty phenotype of exhaustion;
determining a power score or a moment score from the joint angular velocity and the joint angular acceleration, the power score or moment score reflecting a frailty phenotype of weakness; and
determining the frailty index of the person based on at least on a combination of the determined scores reflecting the frailty phenotypes of flexibility, slowness, exhaustion, and weakness, and displaying an indication of the determined frailty index.

39. The non-transitory computer storage of claim 38, wherein the computer hardware is further directed to at least:
receive or determine anthropometric data of the person; and
determine the frailty of the person based at least on the first variable comprise further determining the frailty of the person based on the anthropometric data of the person.

40. The non-transitory computer storage of claim 38, wherein determining the at least one frailty marker comprising slowness, weakness, exhaustion, or flexibility comprises determining speed of the movement, reduction in speed of the movement over a predetermined period of time, flexibility in the movement, power of the movement, rise time of the movement, number of the movement over the predetermined period of time, jerkiness of the movement, and moment of the movement.

41. The non-transitory computer storage of claim 38, wherein the determining the at least one frailty marker comprises determining:
the slowness based on speed and rise time of the movement,
the weakness based on power and moment of the movement,
the exhaustion based on speed reduction and jerkiness of the movement, and
the flexibility based on magnitude of joint motion of the movement.

42. The non-transitory computer storage of claim 41, wherein
a frailty status associated with the person is determined based on the at least one frailty marker, and
the frailty status comprises a non-frail status, a pre-fail status, and a frail status.

43. An improved method for determining and stratifying a frailty index of a person into categories, the method comprising:
generating one or more movement signals by at least one movement sensor, the at least one movement sensor being configured to measure movement of a limb of the person;
determining a first variable associated with the movement of the limb of the person based on sensor data derived from the one or more movement signals generated by the at least one movement sensor, the at least one movement sensor being a multi axial inertial sensor configured to measure or determine angular velocity of a limb about a joint, the determining including implementing an algorithm for analyzing body segment movement using signals from the at least one movement sensor, the algorithm further determining other variables associated with limb movement using differentiation or integration or both; and
determining the frailty index of the person based at least on the first variable and the determined other variables, wherein the first variable comprises a joint angular velocity associated with the movement of the limb over a predefined interval of time, the determining the frailty index comprising:
deriving a joint angular acceleration or a joint angular flexion angle from the joint angular velocity, and determining one or more of a flexibility score, a speed score, a rise time score, a speed reduction score, a jerkiness score, a power score, or a moment score,
wherein the flexibility score is based on the joint angular flexion angle over the predefined interval of time, the flexibility score reflecting a frailty phenotype of flexibility;
wherein the speed score or the rise time score is based on the joint angular velocity over the predefined interval of time, the speed score or rise time score reflecting a frailty phenotype of slowness;

wherein the speed reduction score or the jerkiness score is based on the joint angular velocity over the predefined interval of time, the speed reduction score or jerkiness score reflecting a frailty phenotype of exhaustion;

wherein the power score or the moment score is based on the joint angular velocity and the joint angular acceleration, the power score or moment score reflecting a frailty phenotype of weakness; and determining the frailty index of the person based on at least on a combination of one or more of the determined scores reflecting the frailty phenotypes of flexibility, slowness, exhaustion, or weakness, and displaying an indication of the determined frailty index.

* * * * *